(12) United States Patent
Rahimian

(10) Patent No.: US 10,016,619 B2
(45) Date of Patent: Jul. 10, 2018

(54) SYSTEMS AND METHODS FOR TREATING CANCER USING BRACHYTHERAPY

(71) Applicant: Voxel Rad, Ltd., Irvine (CA)

(72) Inventor: Javad Rahimian, Irvine, CA (US)

(73) Assignee: Voxel Rad, Ltd., Irvine, CA (US)

( * ) Notice: Subject to any disclaimer, the term of this patent is extended or adjusted under 35 U.S.C. 154(b) by 179 days.

(21) Appl. No.: 15/081,147

(22) Filed: Mar. 25, 2016

(65) Prior Publication Data
US 2017/0050049 A1 Feb. 23, 2017

Related U.S. Application Data

(63) Continuation of application No. 13/719,968, filed on Dec. 19, 2012, now Pat. No. 9,295,856, which is a
(Continued)

(51) Int. Cl.
*A61M 36/10* (2006.01)
*A61N 5/10* (2006.01)
(Continued)

(52) U.S. Cl.
CPC ............ *A61N 5/1007* (2013.01); *A61B 1/303* (2013.01); *A61B 1/32* (2013.01); *A61B 17/0206* (2013.01);
(Continued)

(58) Field of Classification Search
CPC ....... A61N 2005/0611; A61N 5/1001–5/1084; A61N 2005/1003–2005/1098; A61B 17/42–17/447
See application file for complete search history.

(56) References Cited

U.S. PATENT DOCUMENTS 2,959,166 A 11/1960 Clayton
4,292,960 A 10/1981 Paglione
(Continued)

FOREIGN PATENT DOCUMENTS

WO WO 2011/011731 1/2011

OTHER PUBLICATIONS

Malhotra, Harish K., et al. "Duplicating a tandem and ovoids distribution with intensity-modulated radiotherapy; a feasibility study" from the Journal of Applied Clinical Medical Physics, vol. 8, No. 3, Summer of 2007 in 8 pages.
(Continued)

*Primary Examiner* — Catherine B Kuhlman
(74) *Attorney, Agent, or Firm* — Knobbe Martens Olson & Bear LLP

(57) ABSTRACT

Systems and methods are provided for treating cervical and/or uterine cancers in brachytherapy with an intracavitary brachytherapy applicator. The system comprises a tandem adapted for insertion into a cervix of a patient. An ovoid assembly comprises first and second inflatable ovoids and an ovoid support mechanism. The first and second inflatable ovoids are adapted for insertion within fornices of a patient. First and second retractors are adapted to be coupled to the ovoid assembly. The first retractor is adapted to be positioned to retract the bladder of a patient during treatment. The second retractor is adapted to be positioned to retract the rectum of a patient during treatment. The tandem and the first and second inflatable ovoids are adapted to be coupled to a radioactive source to deliver an implant radiation dose suitable for cancer treatment at a cancerous cervical treatment site in a patient.

18 Claims, 18 Drawing Sheets

Related U.S. Application Data continuation-in-part of application No. 13/386,644, filed as application No. PCT/US2010/043121 on Jul. 23, 2010, now Pat. No. 9,295,491.

(60) Provisional application No. 61/271,774, filed on Jul. 24, 2009.

(51) Int. Cl.
*A61B 1/303* (2006.01)
*A61B 1/32* (2006.01)
*A61B 17/02* (2006.01)
*A61B 17/42* (2006.01)
*A61B 17/00* (2006.01)
*A61B 90/00* (2016.01)

(52) U.S. Cl.
CPC .......... *A61B 17/0218* (2013.01); *A61B 17/42* (2013.01); *A61N 5/1016* (2013.01); *A61B 2017/00557* (2013.01); *A61B 2090/3966* (2016.02); *A61N 2005/1058* (2013.01); *A61N 2005/1059* (2013.01)

(56) References Cited

U.S. PATENT DOCUMENTS

| | | | |
|---|---|---|---|
| 4,294,264 A | | 10/1981 | Fischell et al. |
| 5,012,357 A | | 4/1991 | Schoeppel et al. |
| 5,562,594 A | | 10/1996 | Weeks |
| 6,312,375 B1 | * | 11/2001 | Montebello .......... A61N 5/1016 600/3 |
| 6,482,142 B1 | | 11/2002 | Winkler et al. |
| 6,699,171 B2 | | 3/2004 | Harmon |
| 7,534,202 B2 | | 5/2009 | Eng |
| 7,666,130 B2 | | 2/2010 | Mick |
| 7,678,040 B2 | | 3/2010 | Francescatti et al. |
| 8,500,618 B2 | * | 8/2013 | Isham ................ A61B 17/4241 600/3 |
| 9,295,856 B2 | | 3/2016 | Rahimian |
| 2004/0006305 A1 | | 1/2004 | Hebert et al. |
| 2006/0116546 A1 | | 6/2006 | Eng |
| 2006/0235260 A1 | | 10/2006 | Mourtada et al. |
| 2008/0064916 A1 | | 3/2008 | Mick |
| 2008/0167514 A1 | | 7/2008 | Lim et al. |
| 2009/0171157 A1 | | 7/2009 | Diederich et al. |
| 2010/0048977 A1 | | 2/2010 | Sing et al. |
| 2010/0069878 A1 | | 3/2010 | Parsai et al. |
| 2012/0123188 A1 | | 5/2012 | Rahimian |

OTHER PUBLICATIONS

Medical Physics, AAPM Annual Meeting Issue, Imaging Physics, dated Jun. 1999, vol. 26, No. 6, in 3 pages.
PCT/EP2010/043121 International Search Report, dated Apr. 20, 2011 issued in the name of Voxel Rad, Ltd in 10 pages.
United States Court of Appeals for the Federal Circuit; *Hologic, Inc., Cytyc Corporation and Hologic L.P.* v *Senorx, Inc.*; Decided Feb. 24, 2011 in 21 pages.

* cited by examiner though the bladder or the rectum causing unwanted morbidities in some cases. Accordingly, in order to keep the radiation dose within the respective tolerance doses of the organs at risk, in some cases a user lowers the dose to the tumor; thus potentially causing the cancer to reoccur. Some optimization algorithms are currently used in the HDR treatment planning systems, however these cannot and do not adequately substitute or replace a geometrically optimum implant.

SYSTEMS AND METHODS FOR TREATING CANCER USING BRACHYTHERAPY

CROSS-REFERENCE TO RELATED APPLICATIONS

This application is a continuation of U.S. patent application Ser. No. 13/719,968, filed Dec. 19, 2012, which is a continuation-in-part of U.S. patent application Ser. No. 13/386,644, filed Jan. 23, 2012, which is a national phase application of PCT/US2010/043121, filed Jul. 23, 2010, which claims the priority benefit of U.S. Provisional Application Ser. No. 61/271,774, filed on Jul. 24, 2009, the entirety of each of which is hereby incorporated by reference herein.

BACKGROUND

Field of the Invention

The present application relates to devices and methods for treating cancer using brachytherapy. In particular, the present application relates to devices and methods for treating cervical and/or uterine cancers in brachytherapy with an intracavitary brachytherapy applicator.

Description of the Related Art

"Brachy" is derived from the Greek word "brachio" meaning short range, and in reference to brachytherapy is defined as "Short Range Treatment with a Radioisotope." Five years after $^{226}$Ra was discovered by Marie and Pierre Curie in Paris, Alexander Graham Bell suggested the implantation of radioactive sources directly into the tumors. That same year in 1903, two cases of facial basal cell carcinoma were treated, using $^{226}$Ra surface molds in St. Petersburg.

Brachytherapy typically offers low morbidity by delivering a high dose of ionizing radiation to the target volume, sparing surrounding healthy tissue with rapid dose fall off outside the implanted volume. Selective placement of the radioactive sources allow the dose distribution to be manipulated to match the target shape. Brachytherapy can be used in treating most areas of the body and can be used alone or in conjunction with External Beam Radiotherapy, Chemotherapy, and Surgery for management of cancer. HDR and LDR brachytherapy are well-established techniques with a long history of use in treatment of cervical and uterine cancers. The scientific principle behind this technology is that a highly radioactive source inside an afterloader passes through a transfer guide tube into an applicator implanted in the patient. The radioactive source is programmed to remain in its precise location for a given period to deliver radiation dose according to the prescription. This can be effective in treating cancers of the cervix and uterus.

One known applicator for use in brachytherapy is the Fletcher-Suit-Delclos (FSD) afterloading intracavitary brachytherapy applicator for treatment of cervical and uterine cancers. Intracavitary brachytherapy procedure using FSD applicator for treatment of cervical and uterine cancers is tedious and time consuming. The procedure requires the patient to be consciously sedated or anesthetized as the procedure can be painful and lengthy with the complex design of the current available applicators requiring one to two nurses in assisting the radiation oncologist in implanting the applicator. The non-ideal geometry of the applicator placement, and the inadequate and occasionally painful placement of the vaginal packing retractor used to retract the bladder and the rectum from the plane of the implant, make the radiation dosimetry non-ideal, with high doses reaching the bladder or the rectum causing unwanted morbidities in some cases. Accordingly, in order to keep the radiation dose within the respective tolerance doses of the organs at risk, in some cases a user lowers the dose to the tumor; thus potentially causing the cancer to reoccur. Some optimization algorithms are currently used in the HDR treatment planning systems, however these cannot and do not adequately substitute or replace a geometrically optimum implant.

In recent years many intracavitary applicators based on the FSD applicator concept have been designed, and used in the clinic, e.g., the Week, Williamson, Henschke and Mick applicators. The typical prescription requires 3 or 4 implants, one week apart, on the same patient. The traditional FSD applicator normally consists of 8-pieces assembled as the patient rests supine in the stirrup position. The current clinical procedure using FSD applicator is typically lengthy, painful, and often requires anesthetics, or conscious sedation. The problems outlined herein have made patients request alternative treatments such as surgery or use of Intensity Modulated Radiotherapy (IMRT). However, the intracavitary brachytherapy for treating cervical and uterine cancers should not be replaced with IMRT since intracavitary brachytherapy provides more conformal therapy, less integral dose, and superior sparing of the organs at risk.

SUMMARY OF SOME EMBODIMENTS

The present application relates to devices and methods for treating cervical and/or uterine cancers in brachytherapy with an intracavitary brachytherapy applicator to harness the benefits of brachytherapy in addition to easing and improving the implant procedure. Some embodiments comprise an advanced applicator system built for high and/or low dose rate (HDR and LDR) brachytherapy using a novel and innovative design with the aim of easier implantation of the applicator.

According to some embodiments, an intracavitary brachytherapy applicator has a tandem and first and second inflatable ovoids. The tandem and ovoids are adapted to deliver an implant radiation dose for treatment of a patient. In some embodiments the applicator comprises one or more retractors. The ovoids are preferably coupled to an ovoid assembly to support the ovoids and to control the relative position of the ovoids. The tandem is preferably releasably coupled to the ovoid assembly and is adjustable relative to the ovoid assembly. The tandem preferably pivots and translates relative to the ovoid assembly. The tandem is preferably coupled to the ovoid assembly in a manner that limits or restricts rotation of the tandem about a longitudinal axis of the tandem. In some embodiments retractors are releasably coupled with the ovoid assembly. A first retractor can be positioned to retract the bladder of a patient during treatment and a second retractor can be positioned to retract the rectum of a patient during treatment. The retractors are preferably inflatable to at least partially retract the bladder and rectum from a treatment site. In some embodiments the tandem is preferably integrated with an endoscope to facilitate treatment. Embodiments of the present application provide advantages over the Fletcher-Suit-Delclos (FSD) afterloading intracavitary brachytherapy applicators.

According to one embodiment, an applicator comprises a tandem catheter and comprises two colpostats arranged for introduction of radioactive sources for intracavitary brachytherapy. The tandem can be integrated with an endoscope in some embodiments that gives the capability of locating the cervical os and guiding the tandem into the uterine canal.

The conventional FSD applicator colpostats are made of variously sized rigid caps. According to one embodiment, the applicator comprises two inflatable ovoid balloons with the capability of expansion to multiple sizes through iodinated saline. To replace inadequate retraction offered by currently used vaginal packing, two additional semi-cylindrical balloons are preferably attached to the ovoid assembly for retracting the bladder and rectum to lower the radiation dose received by these organs. The applicator preferably provides a geometrically optimum implant where the tandem is positioned to bisect the ovoids, the ovoids are inflated and positioned to the largest size appropriate to fit the anatomy of the patient, and the bladder and the rectum are pushed away from a plane of the implant by one or more retractors. In some embodiments the retractors push the bladder and rectum away from a plane of the implant by at least two centimeters. The applicator implements inflatable retractors for isolating the patient's bladder and the rectum from radioactive sources, lowering the radiation dosage absorbed by these critical structures. An endoscope integrated with the tandem, in some embodiments, can provide advantages such as, for example, locating the cervical os more easily, limiting uterine perforations, sounding the uterus, and guiding the tandem through the uterine canal.

According to one method, an embodiment of the applicator is provided having a tandem and a dual ovoid assembly. The tandem may have a fiberoptic endoscope integrated with it, so the cervical os can easily be found instead of the patient being blindly poked with a speculum placed in the vaginal canal. The tandem and the collapsed balloon dual ovoid assembly can easily be inserted as a single unit into the vaginal canal. The tandem may be guided by endoscope into the cervical os and uterine canal, where the ovoids may be placed in the cervical fornices. The ovoids can comprise two balloons that are inflated with desired volumes of iodinated saline. The ovoids can conform to the cervical tumor and can provide adaptive brachytherapy. The applicator can allow for the tandem and ovoids to be assembled and/or configured rapidly. Adjustments to the system can be completed outside of the patient, similar to a laproscopy procedure. Advantages of the applicator systems and methods of use include simplification of the use of the implant, utilizing fewer parts, adjustable ovoids fitting the patient fornices with comfort, and the inflatable retraction mechanism to separate and give adequate distance to the bladder and rectum. This will optimize the dose to the cervix and uterus, minimizing the dose to these critical structures.

In some embodiments, advantages of applicator systems and methods may include easier and faster implantation. The applicator can cause less or no pain to the patient. The applicator can reduce complications to the patient. The applicator can have simple and integrated applicator parts. Methods of using the applicator and performing treatments can be reproducible. The applicator can provide improved implant geometry. The applicator can be configured to provide for manipulations to be done outside the vaginal and uterine canals, thus making the implant less invasive and geometrically advantageous. The applicator can provide improved radiation dosimetry and lower dose to bladder and rectum.

According to one embodiment, a system for treating cervical and/or uterine cancers in brachytherapy with an intracavitary brachytherapy applicator comprises a tandem adapted for insertion into a cervix of a patient. The tandem comprises an endoscopic viewing element to facilitate treatment and one or more radiographic markers. An ovoid assembly comprises first and second adjustably inflatable ovoids and an ovoid support mechanism. The ovoid support mechanism is adapted to support the ovoids and to allow for user manipulation to control the relative position of the ovoids for insertion of the ovoids within the fornices of a patient. The first and second adjustably inflatable ovoids have a deflated configuration for insertion into a patient and one or more adjustably inflated configurations for positioning the ovoid assembly during treatment. The first and second ovoids each have one or more radiographic markers. The ovoid assembly comprises a tandem connector adapted to releasably and adjustably couple the tandem to the ovoid assembly to allow for pivotal and translational motion of the tandem relative to the ovoid assembly and to limit rotational movement of the tandem about a longitudinal axis of the tandem. First and second adjustably inflatable retractors are adapted to be releasably coupled to the ovoid assembly at first and second retractor connector portions. The first and second inflatable retractors have a deflated configuration for insertion into a patient and an adjustably inflated configuration for retraction of tissue during treatment. The first retractor is adapted to be positioned to retract the bladder of a patient during treatment and the second retractor is adapted to be positioned to retract the rectum of a patient during treatment. The tandem and the first and second inflatable ovoids are adapted to be coupled to a radioactive source to deliver an implant radiation dose suitable for cancer treatment at a cancerous cervical treatment site in a patient.

According to another embodiment, a system for treating cervical and/or uterine cancers in brachytherapy with an intracavitary brachytherapy applicator comprises a tandem adapted for insertion into a cervix of a patient. An ovoid assembly comprises first and second inflatable ovoids and an ovoid support mechanism. The first and second inflatable ovoids are adapted for insertion within fornices of a patient. First and second retractors are adapted to be coupled to the ovoid assembly. The first retractor is adapted to be positioned to retract the bladder of a patient during treatment and the second retractor is adapted to be positioned to retract the rectum of a patient during treatment. The tandem and the first and second inflatable ovoids are adapted to be coupled to a radioactive source to deliver an implant radiation dose suitable for cancer treatment at a cancerous cervical treatment site in a patient.

According to another aspect, a method of treating cervical and/or uterine cancers in brachytherapy with an intracavitary brachytherapy applicator comprises providing an intracavitary brachytherapy applicator having a tandem, an ovoid assembly comprising first and second inflatable ovoids and an ovoid support mechanism, and first and second retractors adapted to be coupled to the ovoid assembly. The tandem is inserted into a cervix of a patient. The first and second inflatable ovoids are inserted within fornices of a patient. The first and second retractors are inserted within a patient. The first and second inflatable ovoids are inflated within a patient. The bladder of a patient is retracted from a treatment site. The rectum of a patient is retracted from a treatment site. An implant radiation dose suitable for treatment is delivered at a treatment site.

According to another aspect, a method of treating cervical and/or uterine cancers in brachytherapy with an intracavitary brachytherapy applicator can comprise one or more of the following steps. First and second retractors can be coupled to the ovoid assembly prior to insertion within a patient. The tandem and the first and second inflatable ovoids can be coupled to a radioactive source. Retracting the bladder can comprise inflating the first retractor. Retracting the rectum can comprise inflating the second retractor. The tandem can be coupled to the ovoid assembly. The tandem can be translated relative to the ovoid assembly. The tandem can be pivoted relative to the ovoid assembly. The tandem can comprise an endoscopic viewing element. A portion of the anatomy of the patient can be viewed with the viewing element upon insertion of the tandem within the patient. Rotational movement of the tandem about a longitudinal axis of the tandem can be limited by a connection between the tandem and ovoid assembly.

According to some embodiments, a system for treating cervical and/or uterine cancers in brachytherapy with an intracavitary brachytherapy applicator comprises a tandem adapted for insertion into a cervix of a patient. An ovoid assembly comprises first and second inflatable ovoids and an ovoid support mechanism. The first and second inflatable ovoids are adapted for insertion within fornices of a patient. The ovoid support mechanism is adapted to support the ovoids and to allow for user manipulation to control the relative position of the ovoids for insertion of the ovoids within the fornices of a patient. The ovoid support mechanism comprises first and second handles wherein the handles are configured to allow for user manipulation to control the relative position of the ovoids using a coarse adjustment mechanism in a first configuration and using a fine adjustment mechanism in a second configuration. First and second retractors are adapted to be coupled to the ovoid assembly. The first retractor is adapted to be positioned to retract the bladder of a patient during treatment and the second retractor is adapted to be positioned to retract the rectum of a patient during treatment. The tandem and the first and second inflatable ovoids are adapted to be coupled to a radioactive source to deliver an implant radiation dose suitable for cancer treatment at a cancerous cervical treatment site in a patient.

According to some embodiments, a system for treating cervical and/or uterine cancers in brachytherapy with an intracavitary brachytherapy applicator comprises a tandem adapted for insertion into a cervix of a patient. An ovoid assembly comprises first and second inflatable ovoids and an ovoid support mechanism. The first and second inflatable ovoids are adapted for insertion within fornices of a patient. The ovoid assembly comprises a tandem connector adapted to releasably and adjustably couple the tandem to the ovoid assembly. The ovoid assembly comprises a first configuration wherein one or more handles coupled to the tandem connector are in an open position and adapted for pivotal and translational movement of the tandem, and a second configuration wherein the one or more handles coupled to the tandem connector are in a closed position and adapted to clamp the tandem connector to limit movement of the tandem. First and second retractors are adapted to be coupled to the ovoid assembly. The first retractor is adapted to be positioned to retract the bladder of a patient during treatment and the second retractor is adapted to be positioned to retract the rectum of a patient during treatment. The tandem and the first and second inflatable ovoids are adapted to be coupled to a radioactive source to deliver an implant radiation dose suitable for cancer treatment at a cancerous cervical treatment site in a patient.

According to some embodiments, a system for treating cervical and/or uterine cancers in brachytherapy with an intracavitary brachytherapy applicator, comprises a tandem adapted for insertion into a cervix of a patient. An ovoid assembly comprises first and second inflatable ovoids and an ovoid support mechanism. The first and second inflatable ovoids are adapted for insertion within fornices of a patient. First and second retractors are adapted to be coupled to the ovoid assembly. The first retractor is adapted to be positioned to retract the bladder of a patient during treatment and the second retractor is adapted to be positioned to retract the rectum of a patient during treatment. The first and second retractors are adapted to be releasably coupled to the ovoid assembly. The first and second retractors have attachment mechanisms comprising spring actuated lock mechanisms adapted to provide for adjustment of the position of the retractor and to provide for a snap fit connection with the ovoid assembly. The tandem and the first and second inflatable ovoids are adapted to be coupled to a radioactive source to deliver an implant radiation dose suitable for cancer treatment at a cancerous cervical treatment site in a patient.

Still other aspects, features, and attendant advantages of the present application will become apparent to those skilled in the art from a reading of the following detailed description of embodiments constructed in accordance therewith, taken in conjunction with the accompanying drawings. Aspects, features, and attendant advantages of the present application provide improvements over known devices, systems and methods. Some devices, systems and methods related to brachytherapy are described in more detail in the following references, each of which is hereby incorporated by reference herein in its entirety. 1. J. Rahimian, Y. Qian, R. Kagan, Effects of Applicator Spatial Placement Variations on Cumulative Dose to Point A in the Treatment of Cervical Cancer with 3 HDR Intracavitary Brachytherapy Treatments. Medical Physics, Vol. 26, No. 6, p. 1142, 1999 (abstract); 2. Faiz M. Khan The Physics of Radiation Therapy. Third Edition. Lippincott Williams & Wilkins Publishers, 2003; 3. H. K. Malhotra, J. S. Avadhani, S. F. deBoer, et. al. Duplicating a tandem and ovoids distribution with intensity modulated radiotherapy: a feasibility study. J. of Appl. Clin. Med. Phys. Vo. 8, No 3 (2007).

DETAILED DESCRIPTION OF EMBODIMENTS

Figure 1:
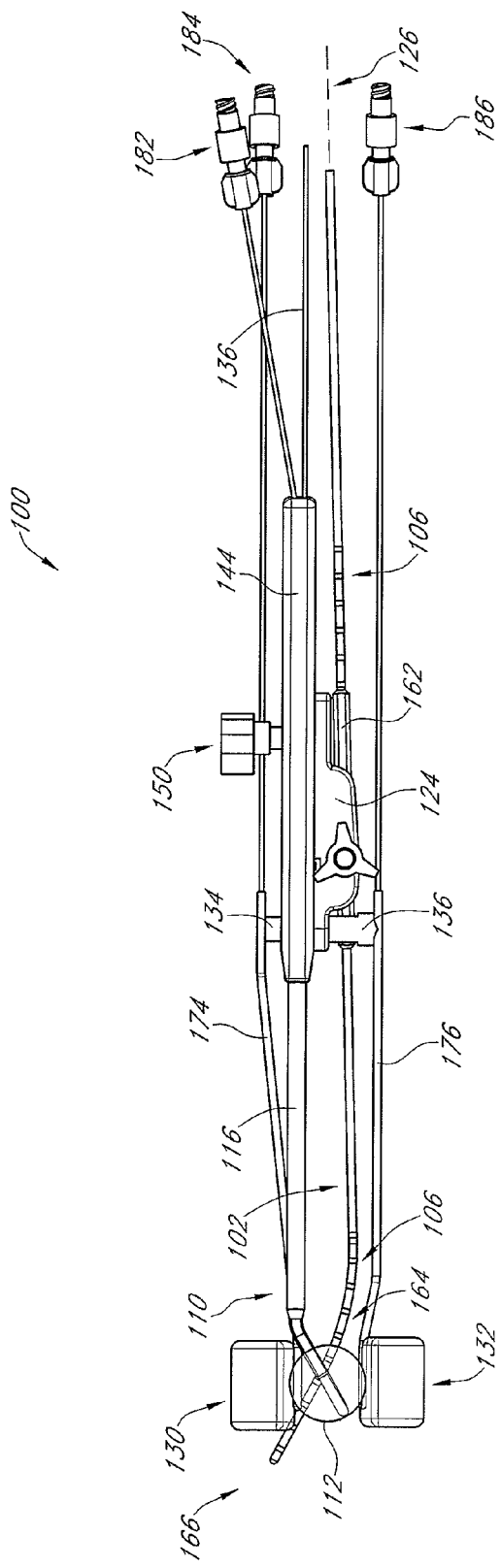
FIG. 1 illustrates a side view of an assembled minimally invasive intracavitary brachytherapy applicator system according to embodiments of the present application.
Figure 2:
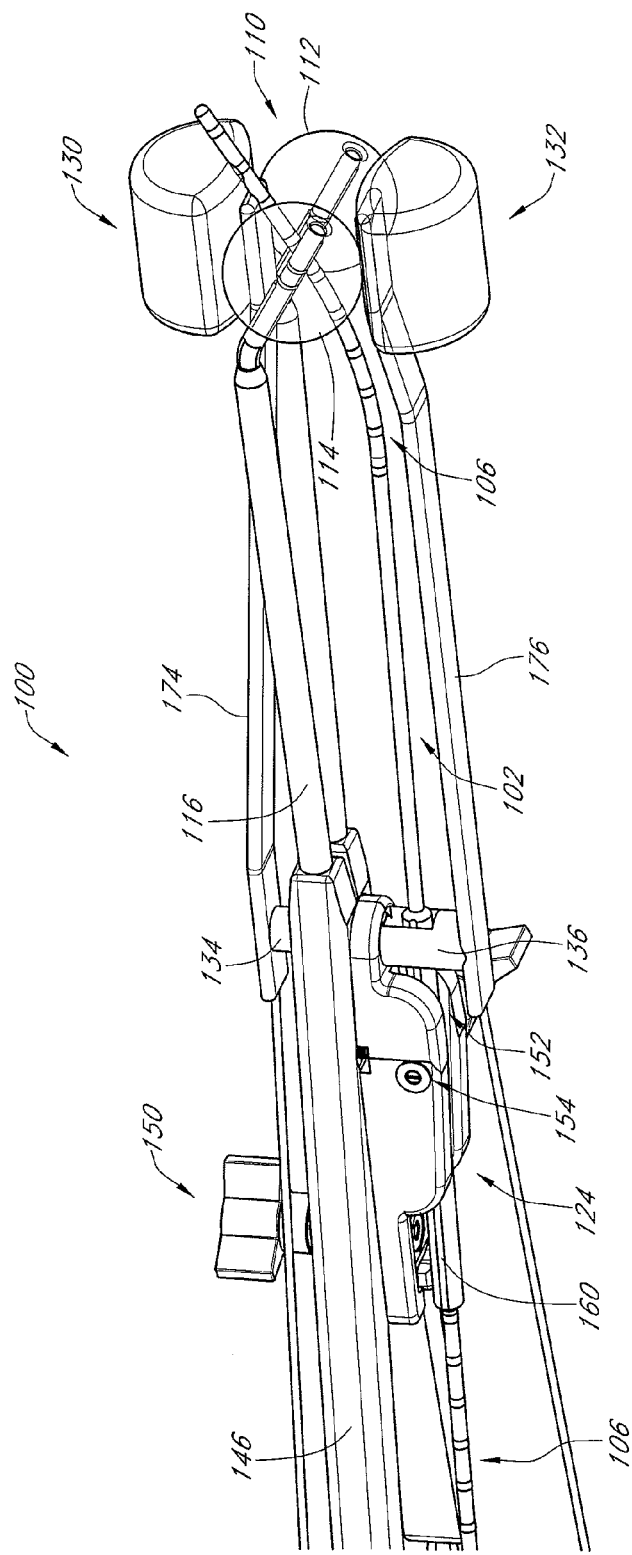
FIG. 2 illustrates a perspective view of a distal portion of the applicator system of FIG. 1 according to embodiments of the present application.
Figure 3:
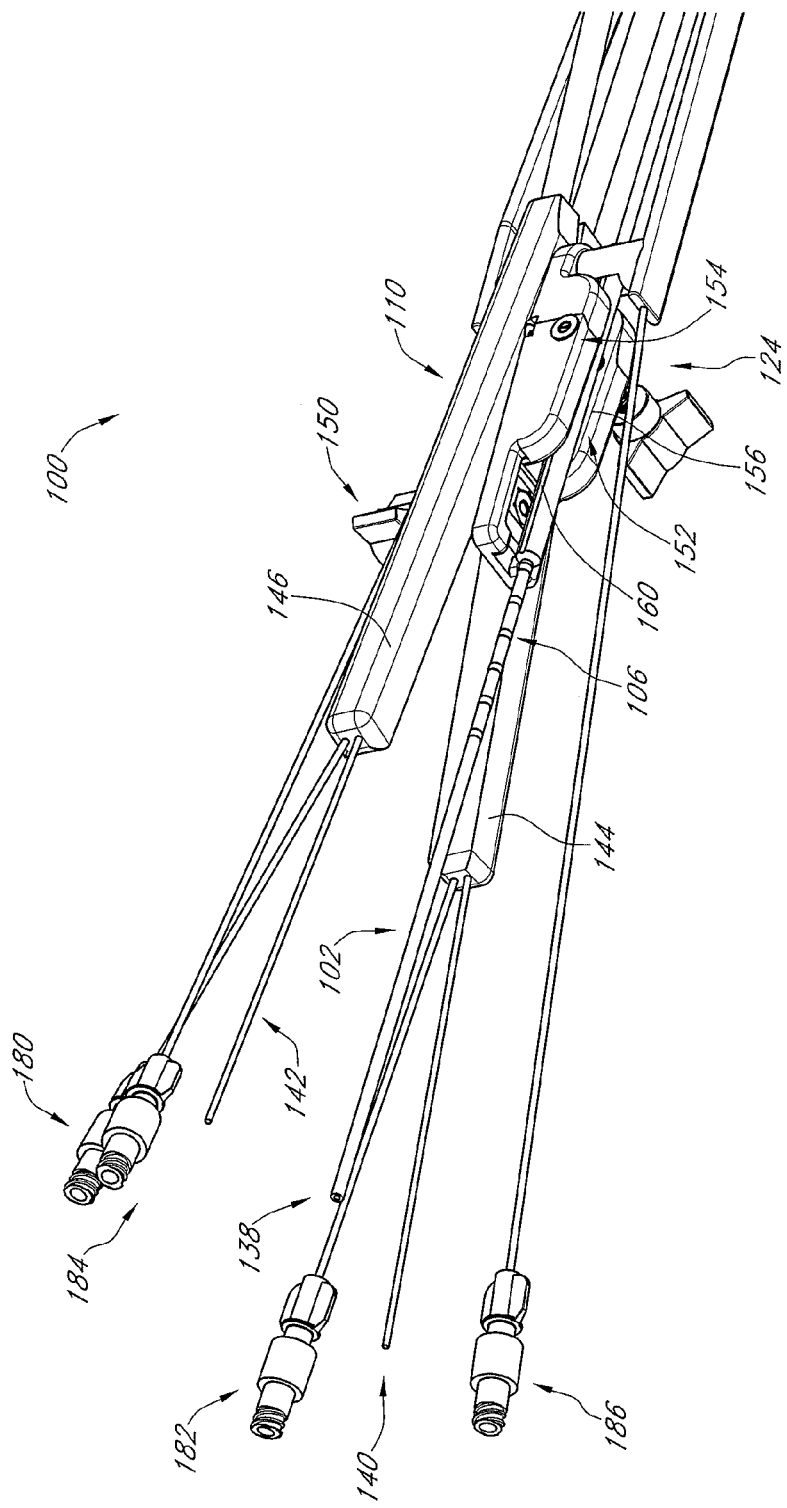
FIG. 3 illustrates a perspective view of a proximal portion of the applicator system of FIG. 1 according to embodiments of the present application.
Figure 4:
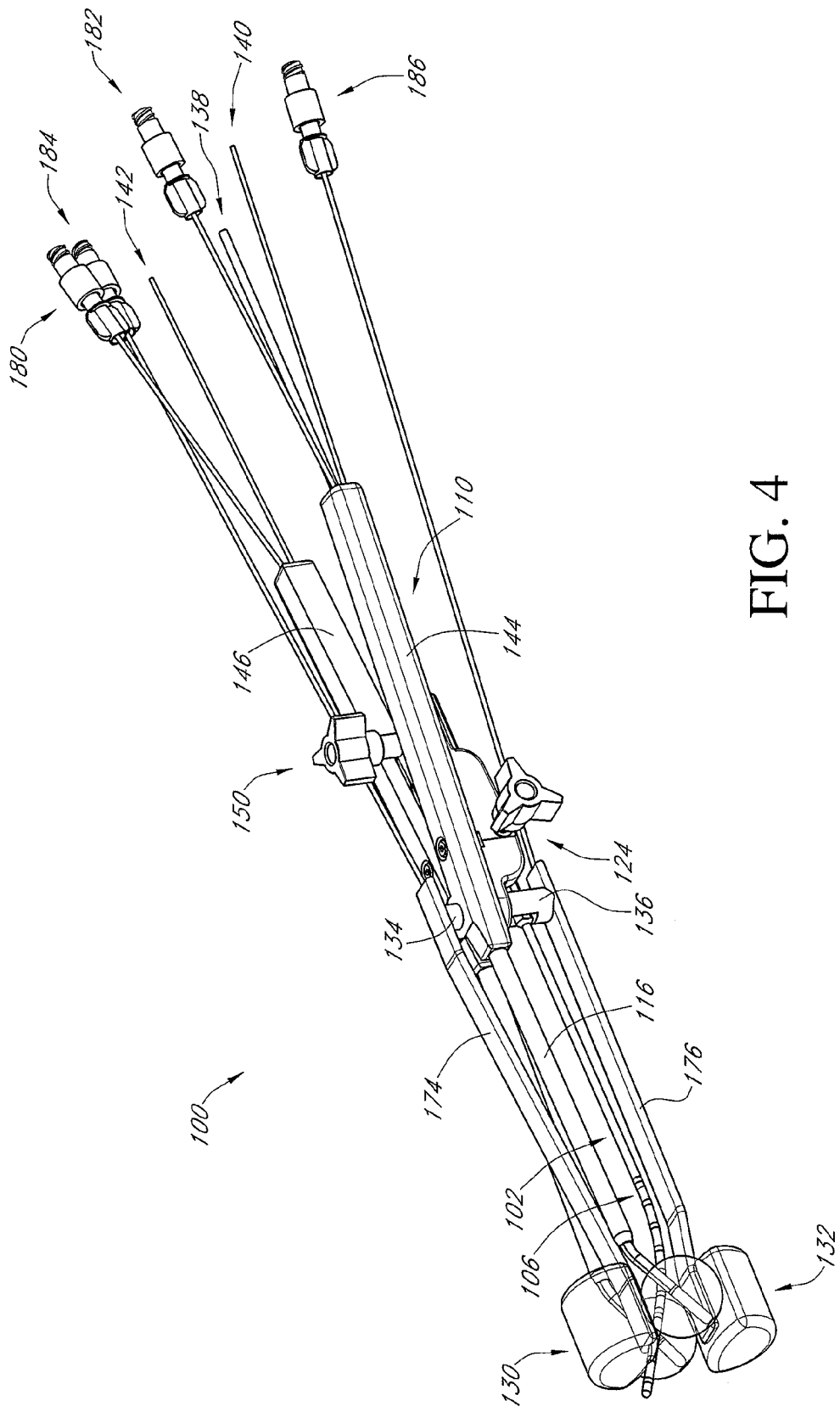
FIG. 4 illustrates a side perspective view of the applicator system of FIG. 1 according to embodiments of the present application.
Figure 5:
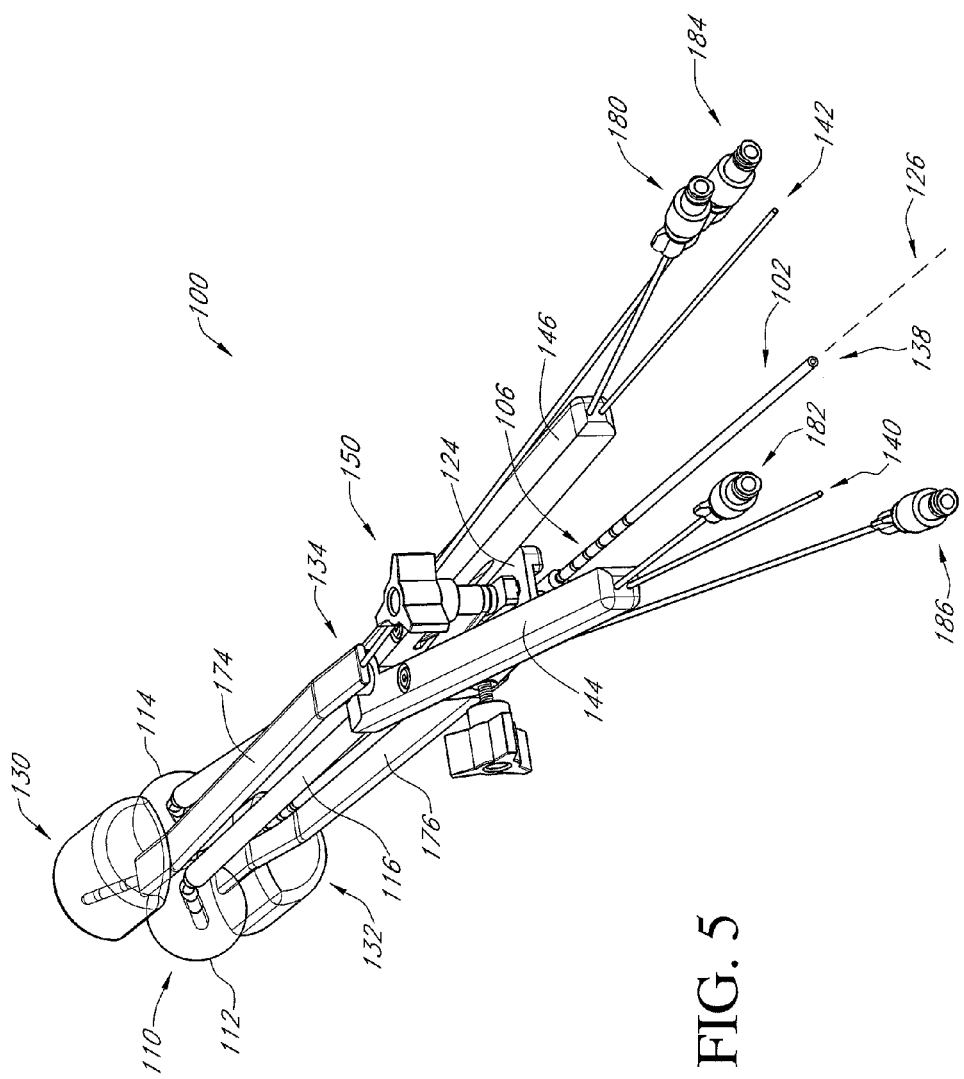
FIG. 5 illustrates a rear perspective view of the proximal portion of the applicator system of FIG. 1 according to embodiments of the present application.
Figure 6:
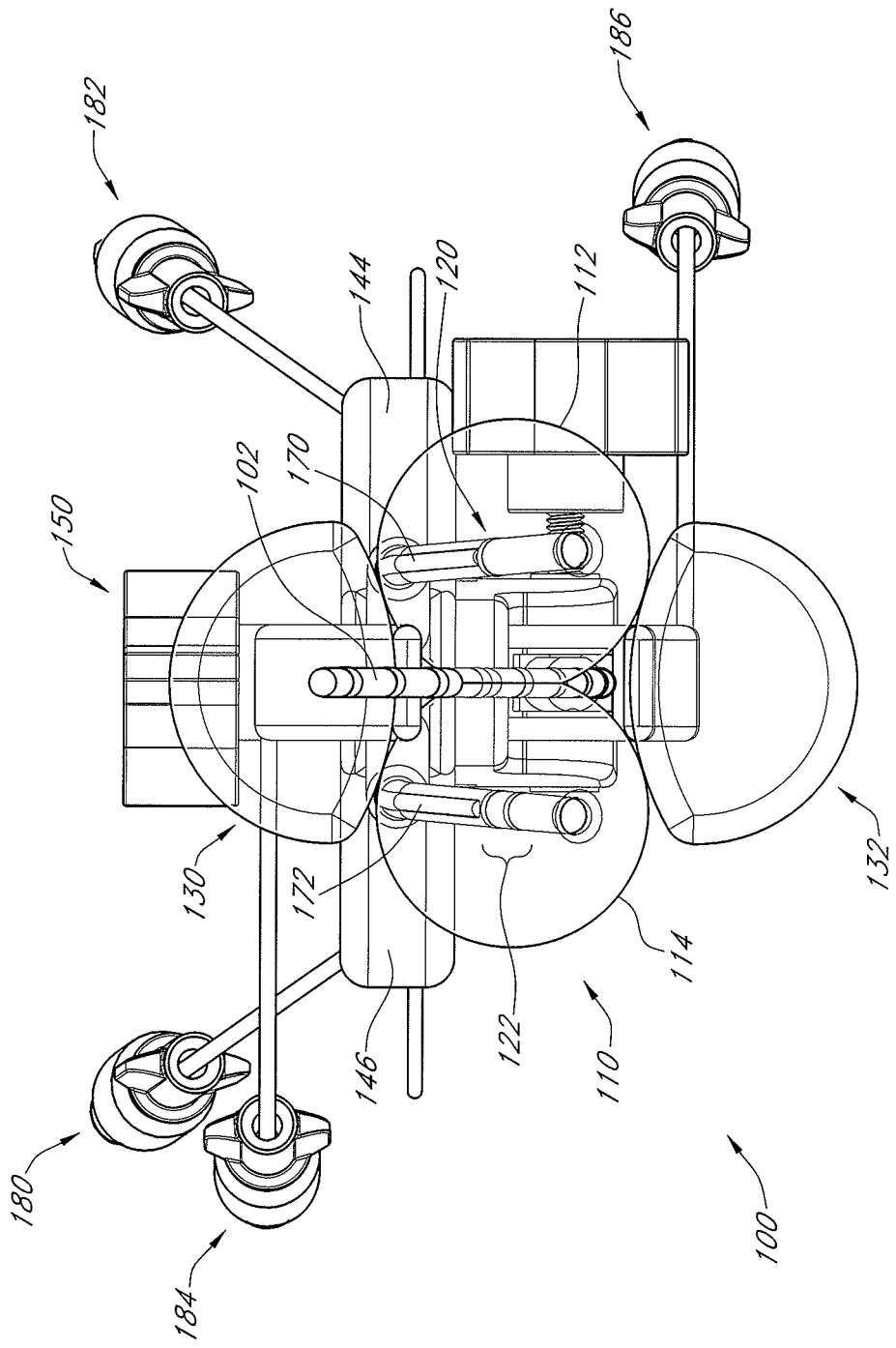
FIG. 6 illustrates a front view of the distal portion of the applicator system of FIG. 1 according to embodiments of the present application.
Figure 7:
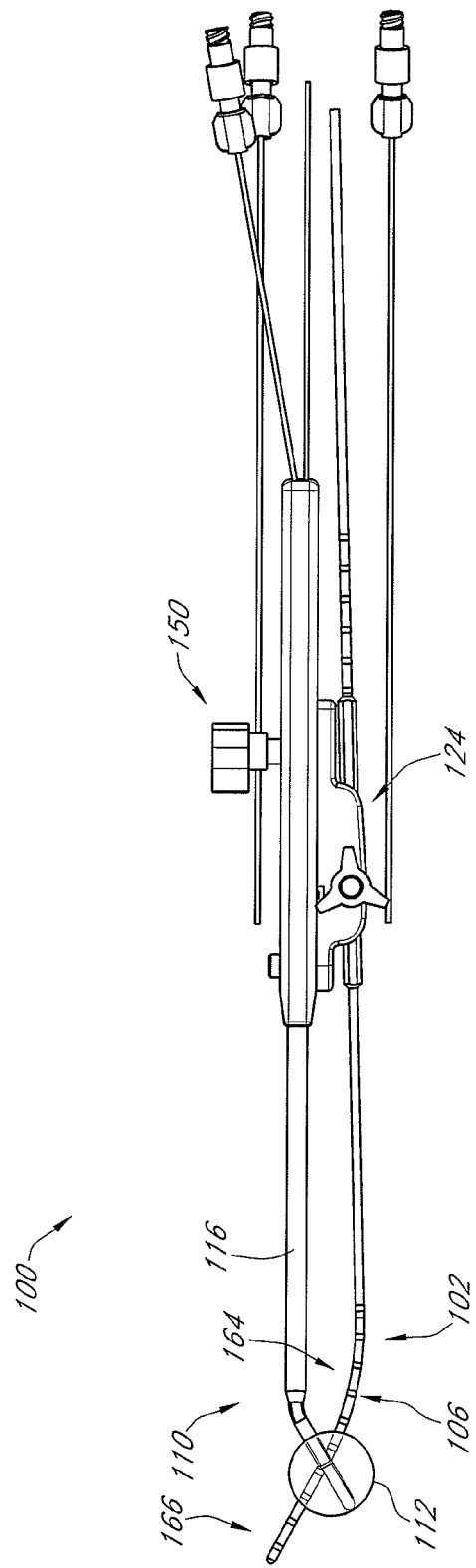
FIG. 7 illustrates a side view of an assembled minimally invasive intracavitary brachytherapy applicator system similar to the system shown in FIG. 1 without the retractor assemblies.
Figure 8:
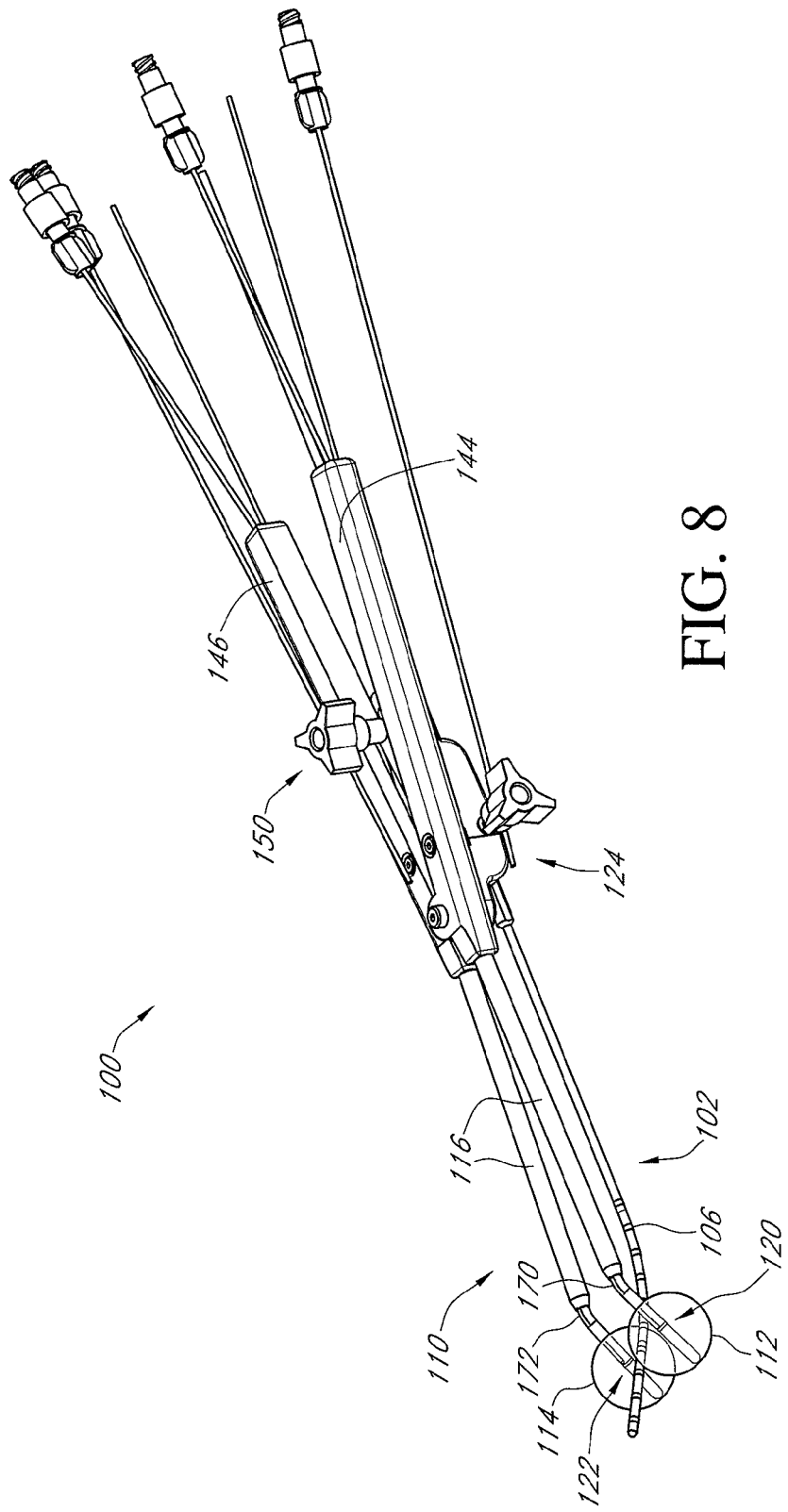
FIG. 8 illustrates a front side perspective view of the applicator system of FIG. 7 according to embodiments of the present application.
Figure 9:
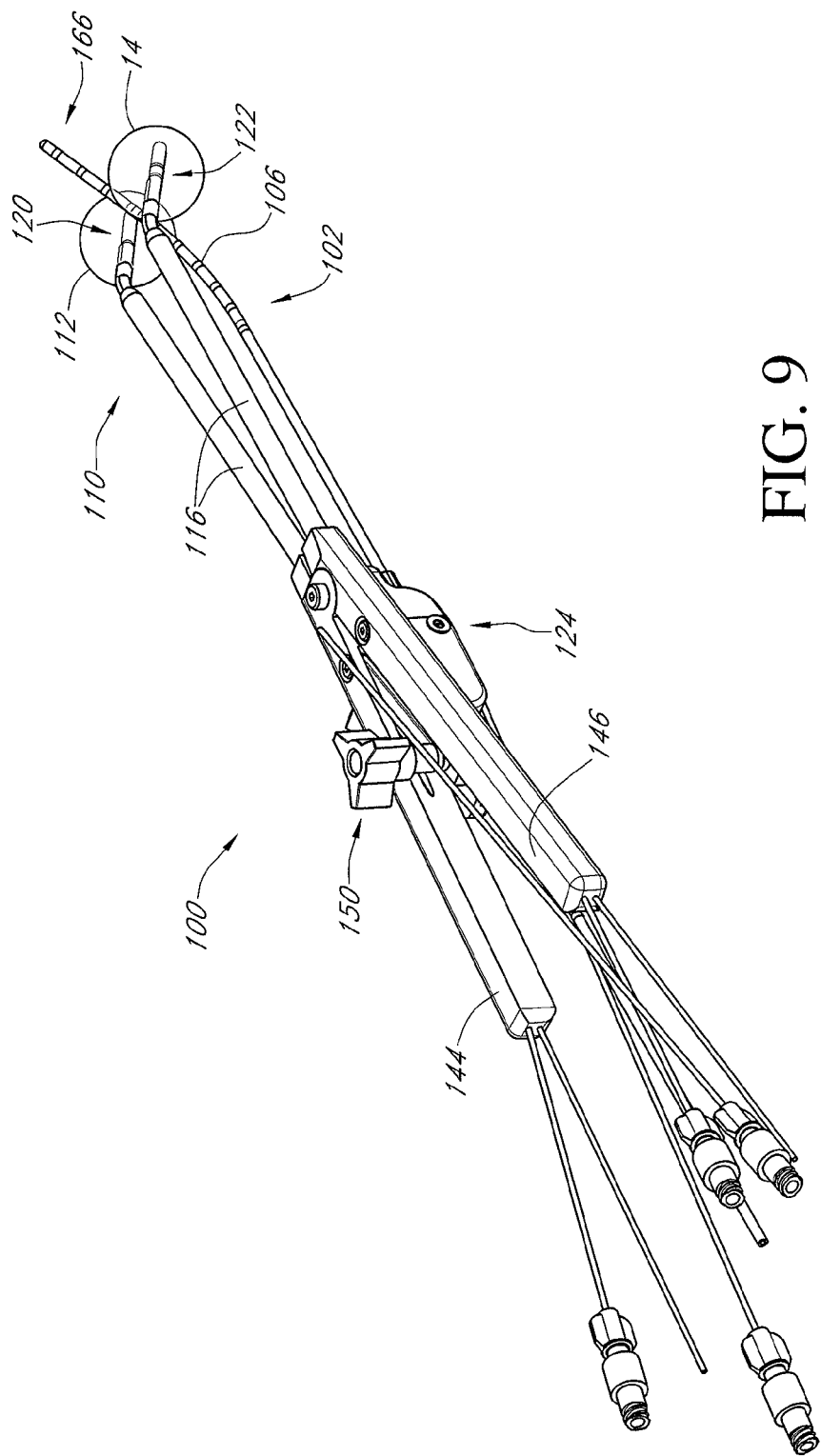
FIG. 9 illustrates a rear side perspective view of the applicator system of FIG. 7 according to embodiments of the present application.
Figure 10:
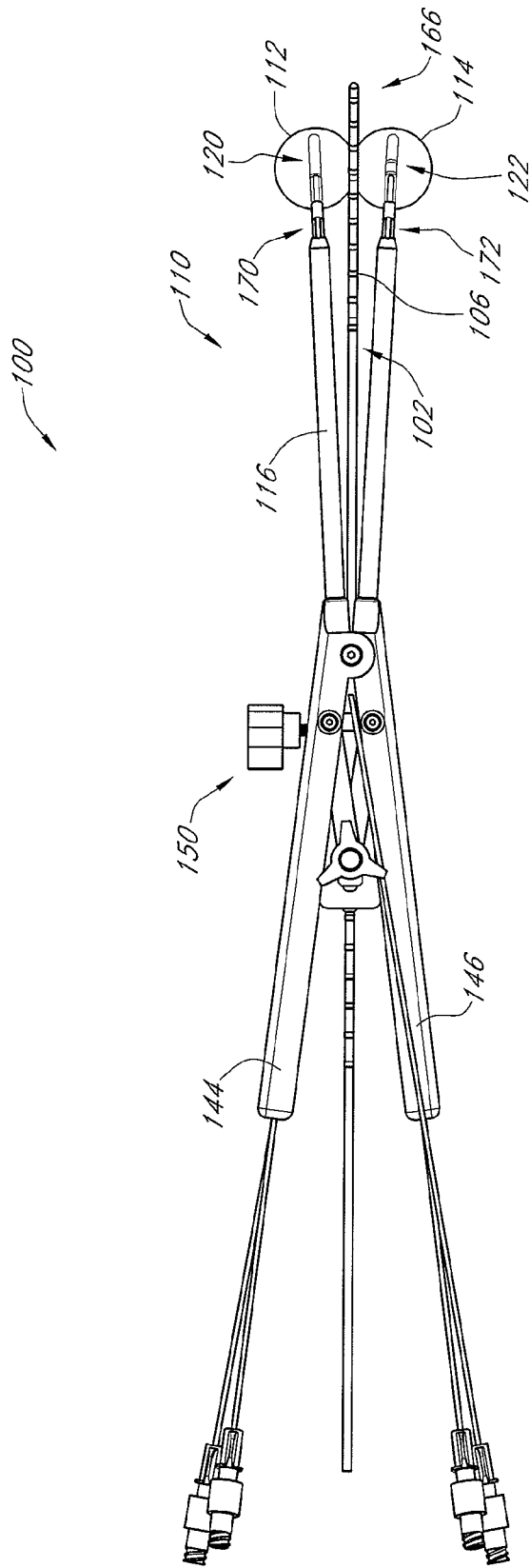
FIG. 10 illustrates a top view of the applicator system of FIG. 7 according to embodiments of the present application.
Figure 11:
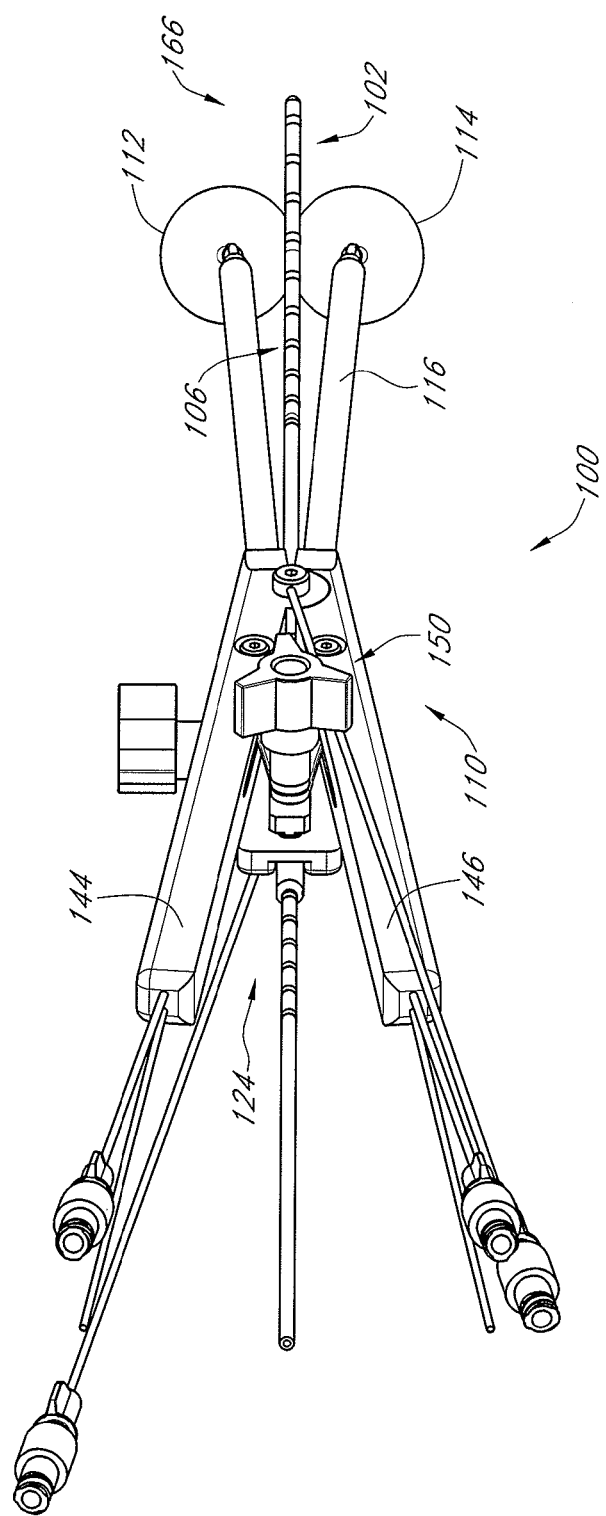
FIG. 11 illustrates a top rear view of the applicator system of FIG. 7 according to embodiments of the present application.
Figure 12:
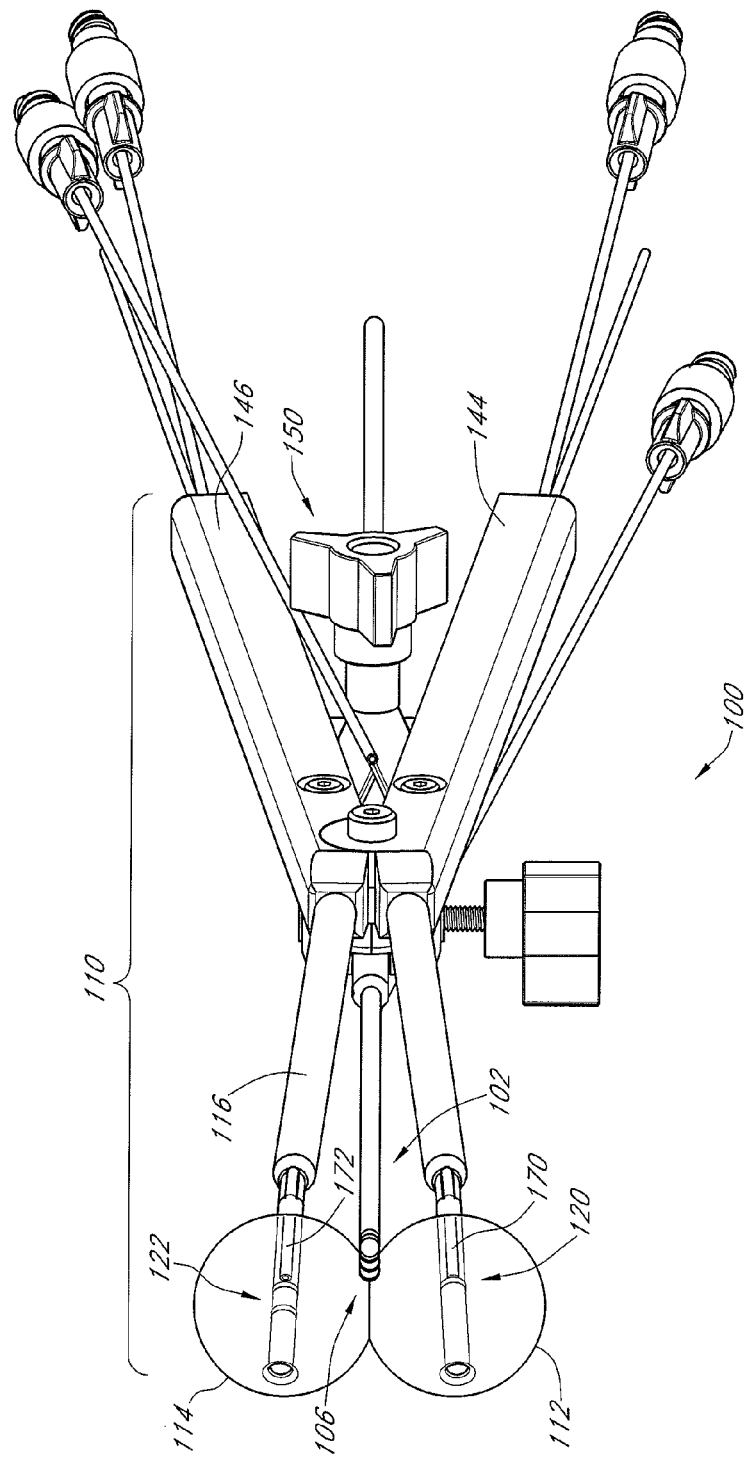
FIG. 12 illustrates a top front view of the applicator system of FIG. 7 according to embodiments of the present application.

The present application relates to devices and methods for treating cervical and/or uterine cancers in brachytherapy with an intracavitary brachytherapy applicator. According to some embodiments, an intracavitary brachytherapy applicator has a tandem and first and second inflatable ovoids. The tandem and ovoids are adapted to deliver an implant radiation dose for treatment of a patient. In some embodiments the applicator comprises one or more retractors. The ovoids are preferably coupled to an ovoid assembly to support the ovoids and to control the relative position of the ovoids. The tandem is preferably releasably coupled to the ovoid assembly and is adjustable relative to the ovoid assembly. The tandem preferably pivots and translates relative to the ovoid assembly. The tandem is preferably coupled to the ovoid assembly in a manner that limits or restricts rotation of the tandem about a longitudinal axis of the tandem. In some embodiments retractors are releasably coupled with the ovoid assembly. In other embodiments retractors can be fixed or attached to the ovoid assembly. A first retractor can be positioned to retract the bladder of a patient during treatment and a second retractor can be positioned to retract the rectum of a patient during treatment. The retractors are preferably inflatable to at least partially retract the bladder and rectum from a treatment site. In some other embodiments the retractors are not inflatable. In some embodiments the tandem is preferably integrated with an endoscope to facilitate treatment.

In some embodiments, an advanced and minimally invasive cervical and uterine HDR and/or LDR applicator system comprises a tandem catheter adapted to be placed inside the uterine canal with two inflatable catheters placed next to the cervical fornices, while using two inflatable semi-cylindrical balloons to retract the bladder and rectum away from the radioactive sources. The tandem central catheter can include endoscopic fiber optics to transmit images of the cervical os, as well as the uterine canal as it is placed. This can facilitate insertion, limit multiple pokes of the cervix, may limit injury to the cervix and uterine perforation causing injury and infection to the uterus as well as to the small bowel. In addition, placement of the applicator is likely to be much faster, preferably on the order of minutes rather than over an hour. The endoscopic tandem and the dual ovoid assembly can be configured as a single piece that advantageously enables the radiation oncologist to implant the applicator possibly without a speculum, reducing pain, anesthetics, and stress on the nursing personnel and the radiation oncologist.

With reference to FIGS. 1-14, according to some embodiments, systems for treating cervical and/or uterine cancers in brachytherapy with an intracavitary brachytherapy applicator 100 comprise a tandem 102 adapted for insertion into a cervix of a patient. The tandem 102 can comprise an endoscopic viewing element 104 to facilitate treatment and one or more radiographic markers 106.

An ovoid assembly 110 comprises first and second adjustably inflatable ovoids 112, 114 and an ovoid support mechanism 116. The ovoid support mechanism 116 is adapted to support the ovoids 112, 114 and to allow for user manipulation to control the relative position of the ovoids for insertion of the ovoids within the fornices of a patient. The first and second adjustably inflatable ovoids 112, 114 have a deflated configuration for insertion into a patient and one or more adjustably inflated configurations for positioning the ovoid assembly during treatment. The first and second ovoids 112, 114 each have one or more radiographic markers 120, 122. The ovoid assembly 110 comprises a tandem connector 124 adapted to releasably and adjustably couple the tandem 102 to the ovoid assembly 110 to allow for pivotal and translational motion of the tandem 102 relative to the ovoid assembly 110 and to limit rotational movement of the tandem 102 about a longitudinal axis of the tandem.

First and second adjustably inflatable retractors 130, 132 are adapted to be releasably coupled to the ovoid assembly at first and second retractor connector portions 134, 136. The first and second inflatable retractors 130, 132 have a deflated configuration for insertion into a patient and an adjustably inflated configuration for retraction of tissue during treatment. The first retractor 130 is adapted to be positioned to retract the bladder of a patient during treatment and the second retractor 132 is adapted to be positioned to retract the rectum of a patient during treatment. The tandem 102 and the first and second inflatable ovoids 112, 114 are adapted to be coupled to a radioactive source to deliver an implant radiation dose suitable for cancer treatment at a cancerous cervical treatment site in a patient.

Some embodiments are described in more detail below. The applicator systems and methods can have one or more of the following advantageous characteristics in some embodiments.

Applicator Assembly

Some embodiments include applicator systems 100 that can be pre-assembled before insertion into the patient such that only a few, and in some cases, preferably one or two adjustable and integrated pieces are inserted into the patient. In contrast, the current FSD applicators require about 8 pieces to be assembled while inserted within a patient during use. Accordingly, use of embodiments of the present application preferably makes insertion and manipulation of the implants faster, more dosimetrically optimal, lessens the need for anesthetics, and reduces pain to the patient.

Ovoid Assembly

As shown in FIGS. 1-12, the applicator system 100 comprises a pair of ovoids 112, 114 in the form of inflatable balloons, each with varying volume capacity, rather than solid caps of varying sizes currently used as colpostats. The inflatable balloon ovoids 112, 114 can advantageously and naturally take on the shape of mini, small, medium, and/or large size ovoids depending on the size of the patient's anatomy. In some embodiments, the ovoids 112, 114 can be independently inflated to 4 different sizes of the following approximate dimensions:

| SIZE | WIDTH | LENGTH | VOLUME |
|---|---|---|---|
| Mini | 1.4 cm | 3.0 | 5 cc |
| Small | 2.0 cm | 3.0 | 10 cc |
| Medium | 2.5 cm | 3.0 | 15 cc |
| Large | 3.0 cm | 3.0 | 21 cc |

Depending on the patient's anatomy, and the extent, and the size, and the side of the gross disease, the two ovoids 112, 114 can be inflated with different volumes. For example, one ovoid can be inflated as small size and the other as medium size ovoid. The left and the right side ovoids are preferably substantially identical in size, even though at the radiation oncologist's and/or the physicist's discretion, one can be inflated larger than the other depending on the extent of the disease and size of the fornices. In some other embodiments the ovoids can have different maximum sizes.

As described above and as shown in FIGS. 1-12, the ovoid support mechanism 116 is adapted to support the ovoids 112, 114 and to allow for user manipulation to control the relative position of the ovoids for insertion of the ovoids within the fornices of a patient. The ovoid support mechanism 116 supports first and second catheter shafts 140, 142 coupled with the ovoids for delivering radiation to the ovoids. The ovoid support mechanism also comprises first and second handle portions 144, 146 coupled for pivotatal movement relative to one another. Movement of the handle portions 144, 146 relative to each other controls the distance between the first and second ovoids 112, 114. The relative position of the handle portions 144, 146 can be fixed by tightening a knob 150 at an upper portion of the ovoid support mechanism 116. A lower portion of the ovoid support mechanism 116 comprises the tandem connector 124. The tandem connector 124 comprises a slot 152 for receiving the tandem 102, a spring loaded ball or pin 154 on a first side of the slot 152 and a flat surface 156 on a second side of the slot 152. The tandem 102 comprises a groove 160 for translationally and pivotally coupling to the spring loaded ball or pin 154 when the tandem is positioned in the slot 152. A flat surface 162 of the tandem is positioned opposite the groove 160 and interfaces with the flat surface 156 of the tandem connector 124 when the tandem is positioned in the slot 152 to limit rotational movement of the tandem 102 about a longitudinal axis.

Tandem

Tandems 102 can have different shapes and configurations. For example, some embodiments include tandems having a curved portion 164 of 0, 15, 30, 45, and 60 degrees. The tandem 102 can be provided with or without endoscopic capabilities. Additionally, a tandem 102 can include radiographic markings, for example, one-cm markings, on it for measurement and/or viewing. The markers 106 can be positioned near the tandem tip 166 and/or near the tandem connector portion 124. The tandem 102 and the ovoids 112, 114 are coupled to catheter shafts 138, 140, and 142, respectively. The total internal length of the catheters 138, 140, and 142 are preferably substantially identical for both the tandem 102 and the ovoids 112, 114. In some other embodiments, the total lengths can vary. The internal length of the catheter shafts 138, 140, 142 of the tandem 102 and the two ovoids 112, 114 is preferably about 35 cm. Longer or shorter catheter lengths are also contemplated.

Tandem Coupling

Figure 13:
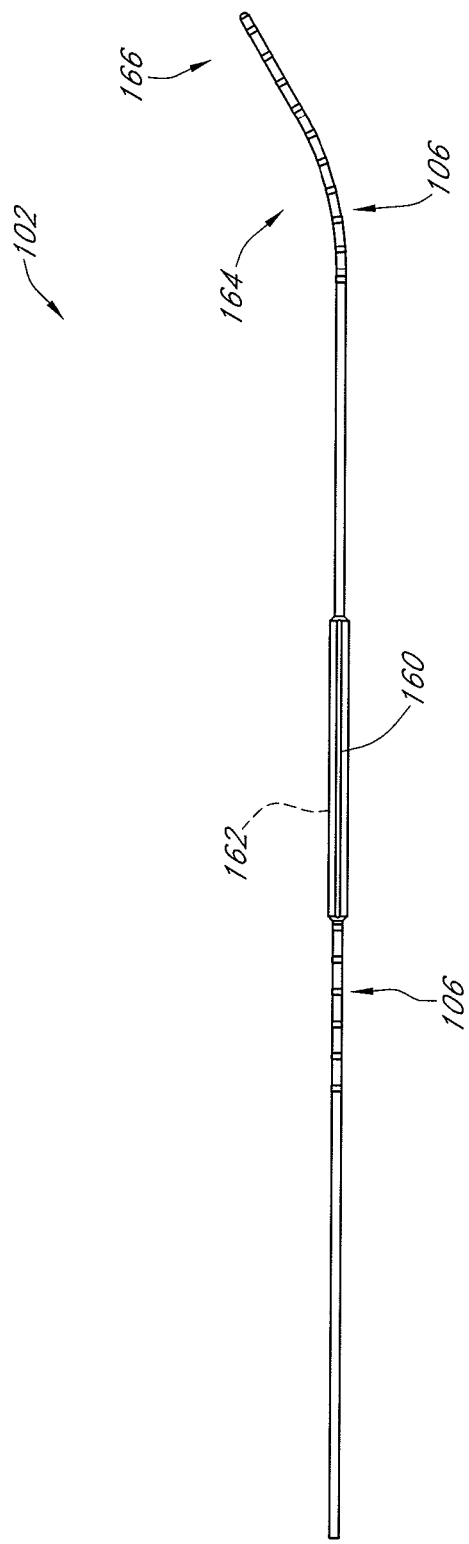
FIG. 13 illustrates a tandem portion of an applicator system according to embodiments of the present application.

As mentioned above, a tandem connector 124 mechanism is provided for coupling the tandem 102 with the ovoid assembly 110. The mechanism preferably enables the tandem 102 to pivot in the anterior/posterior direction about a point in reference to the ovoids 112, 114 using a spring-loaded ball bearing 154 within the ovoid assembly 110 to interface with a groove 160 on a side of the tandem as best seen in FIG. 13. The mechanism also preferably allows the user to translate and/or pivot the tandem to keep it at the mid-plane of the ovoids 112, 114 during treatment. Enabling the user to position the tandem 102 to bisect the ovoids 112, 114 helps to improve implant geometry and dose distribution. In some embodiments, a side of the tandem opposite the grooved side preferably has a flattened surface 162 that contacts a flattened surface 152 of the ovoid assembly 110 to limit inadvertent rotation of the tandem 102 during manipulation and treatment. Accordingly, the mechanism preferably limits the tandem from rotation around a longitudinal axis of the tandem and permits translational and pivotal motion to achieve an advantageous mid-plane position relative to the ovoids 112, 114.

Retractors

Retractor balloons 130, 132 are preferably added to the intracavitary brachytherapy applicator to retract the bladder and the rectum from the radiation sources, thus lowering the dose to these critical structures. This can reduce, and in some cases eliminate, the need to use of vaginal packing after the applicator is in place. The retractor balloons 130, 132 are coupled to catheters 184, 186 that are preferably anchored on the ovoid assembly 110. The retractor balloons 130, 132 are preferably inflated with saline. Other suitable inflation mediums can also be used. The balloons can be semi-cylindrical or semi-ellipsoide when inflated to push the vaginal mucosa, bladder, and rectum away from the radiation site. Balloons having other suitable shapes and sizes for providing retraction can also be used. The retraction mechanism is preferably inflatable to retract the bladder and the rectum by at least about 2 cm away from a plane of the implant defined at the plane of the tandem bisecting the ovoids. The retraction mechanism preferably retracts equidistance from the plane of the implant. The retraction mechanism comprises balloons 130, 132 and retractor supports 174, 176 coupled to the ovoid assembly 110 at retractor connection portions 134, 136.

Materials

The applicator system 100 can comprise environmentally friendly, disposable and/or recyclable materials. For example, plastics such as Delrin, Peek, GlassPeek, etc. can be used. Stainless steel or other suitable materials can be used. In some embodiments, use of allergy causing materials such as latex can be avoided. Balloon materials are preferably very strong, such as, for example, a double-layered polyurethane to avoid leaking and/or bursting. In some embodiments, the applicator is made of MRI and CT friendly materials.

Markers

As discussed above, radiographic markers can be provided along the catheters. Radiographic markers can be used to identify left and right ovoids 112, 114 by varying the number or style of markings 120, 122 on each ovoid. Radiographic markers can be provided on the external surfaces of the ovoid balloons 112, 114 to identify their placements and ensure proper expansion while being treated. Radiographic markers 106 can be provided on the tandem spaced one-cm apart to measure the length of the tandem 102 and/or to measure the magnification factor on the orthogonal radiographs. The applicator system preferably is adapted to be gamma ray, and gas sterilizable. The catheters of the applicator are preferably numbered and marked as corresponding to 1. Right Ovoid catheter 170, 2. Left Ovoid catheter 172, 3. The Luer Lock 182 inflating the Right Ovoid, 4. The Luer Lock 180 inflating the Left Ovoid, 5. The Luer Locks 184, 186 to inflate the retraction mechanism—one for the bladder and one for the rectum.

Guide Tubes

In some embodiments, the applicator 100 can be connected via three equal length transfer guide tubes or catheters 138, 140, 142 to the high dose brachytherapy afterloader with a 192-Iridium High Dose Rate (HDR) radioactive source. In some embodiments the transfer guide tubes 138, 140, 142 can vary in length. The three transfer guide tubes 138, 140, 142 are coupled to the tandem 102 and the pair of inflatable ovoids 112, 114.

Radiation Treatment Modifications

In some embodiments, for Low Dose Rate (LDR) brachytherapy a similarly designed applicator can be used with either 137-Cs tubes or 192-Iridium ribbons (192Ir seeds on a wire) placed inside plastic transfer guide tubes 138, 140, 142. The internal diameters of the tandem and the ovoids will be adjusted relative to the HDR applicator design to accommodate the commercially available 137-Cs tubes. For 192-Iridium ribbons the same tandem and ovoids designed for HDR can be used without any modifications to the internal diameter of the tandem and the ovoid catheters. Other parameters and characteristics of the applicator can be similar to those described for the HDR applicator. The LDR and HDR isodose distributions are preferably similar to the conventional FSD tandem and ovoids implants, yielding similar doses to the treatment site.

Endoscope Assembly

Figure 14:
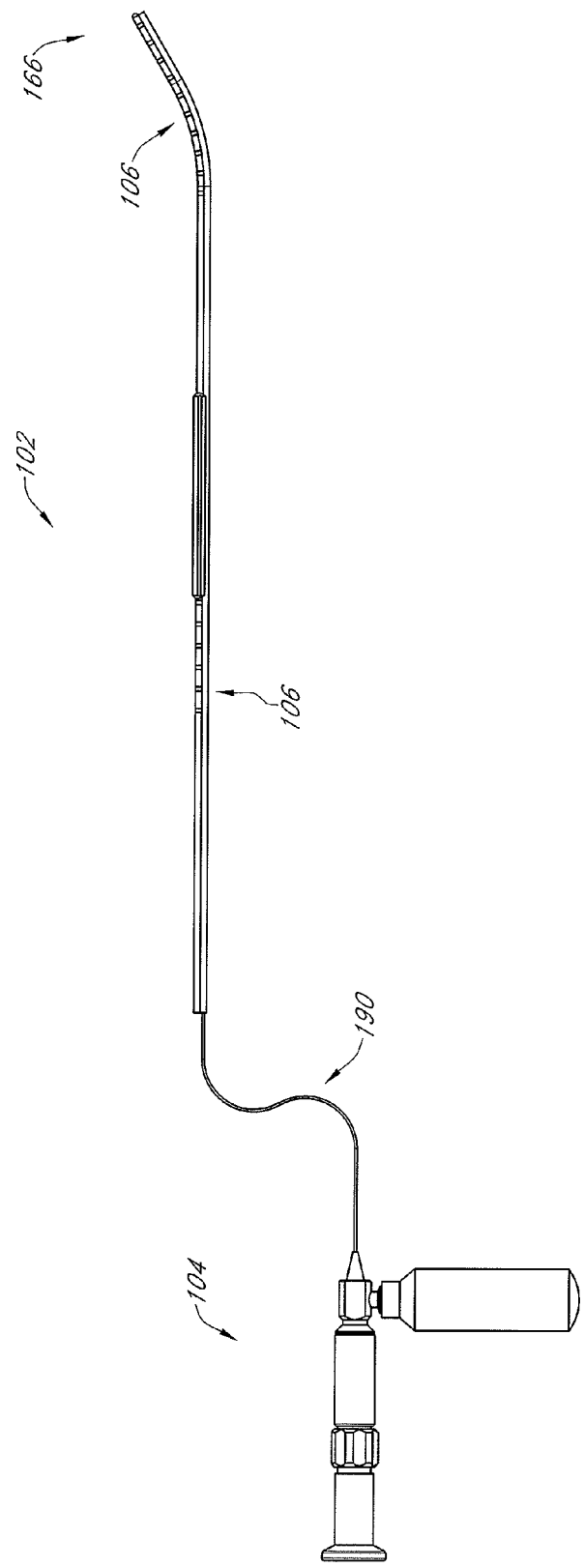
FIG. 14 illustrates an endoscopic tandem portion of an applicator system according to embodiments of the present application.
Figure 15:
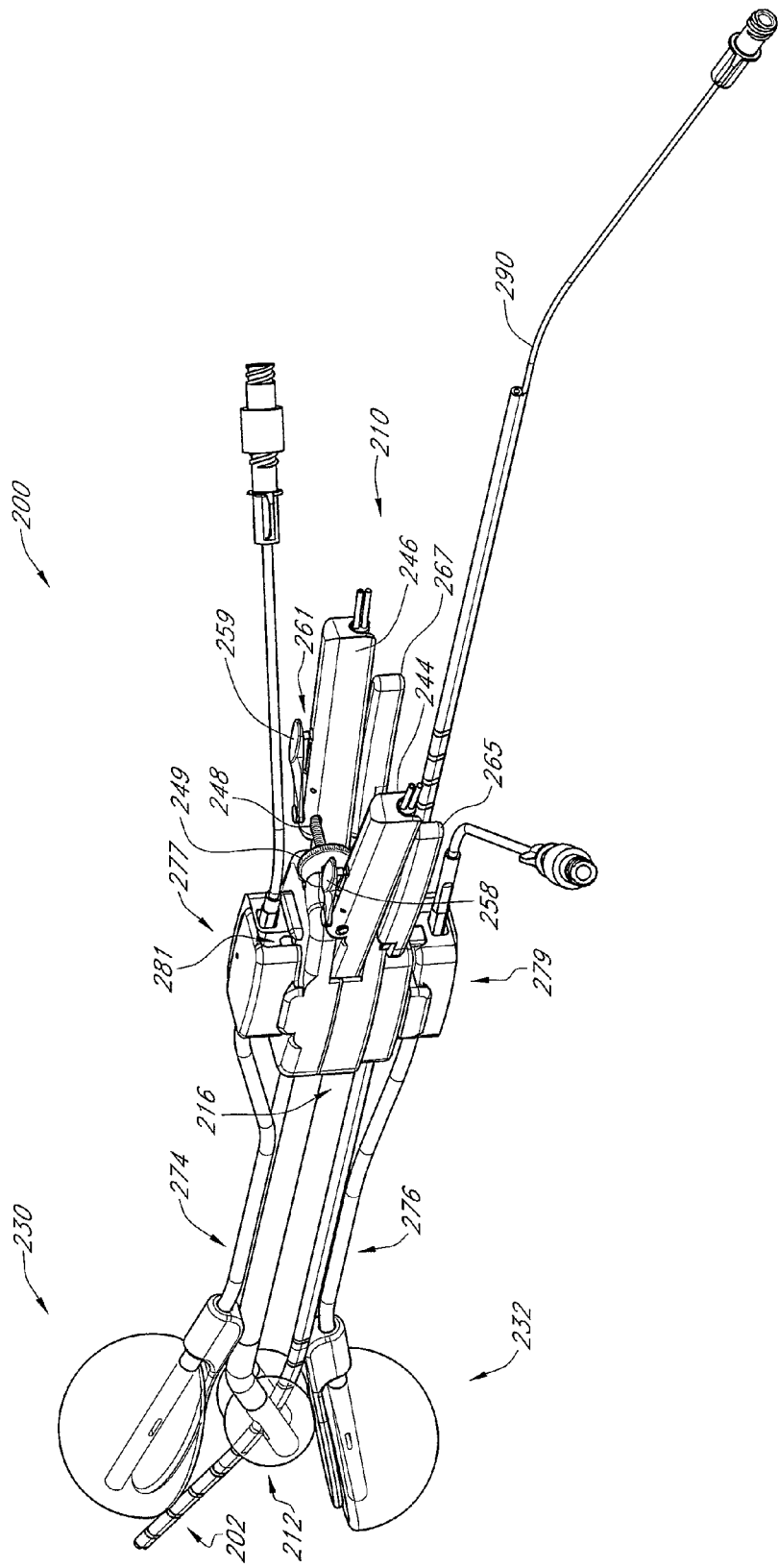
FIG. 15 illustrates a side perspective view of another assembled minimally invasive intracavitary brachytherapy applicator system according to embodiments of the present application.

With reference to FIG. 14, in some embodiments, a miniaturized endoscopic fiber optic bundle 190 is integrated with the tandem 102. In some embodiments, the fiber optic bundle 190 can be about 1 mm thick along the length of the tandem 102. The endoscope 104 can be illuminated by a battery operated LED light and connected to a CMOS or CCD camera. The images preferably can be seen on a display monitor or be captured in a laptop computer connected through a USB2 connector, or other suitable connector, for further analysis. The eye piece can be attached to a coupler that can be attached to a CMOS or CCD camera and connected to a laptop computer or a display monitor. Endoscopic capabilities of the tandem 102 enables the physician to find the cervical os, guide the tandem into the cervical os and uterine canal, sound the uterus, and inspect the extent of the disease in vagina, cervix, uterine canal, and the uterus. The endoscope 104 can help the radiation oncologist to guide the tandem to the end of the uterine canal without perforating it. A mechanism, such as markings on the tandem 106, can be used to measure the length of the uterine canal from the cervical os to the end of the canal. This feature helps sound the uterine canal and position the flange on the tandem to limit the risk of the tandem perforating the uterus.

Methods of Use

In some embodiments, the applicator 100 comprises a tandem catheter adapted to be placed in the uterine canal with a cervical os stopper (e.g., a flange with a ring radiographic marker). The ovoid and retractable system assembly (collectively, ORSA) is preferably coupled prior to treatment to form an integrated unit as one part. The ORSA can be inserted after the tandem is in place. The tandem preferably slides through a central pivoting tract between the two ovoids of the ORSA. The ORSA is inserted inside the vaginal canal until it reaches the cervical fornices. A separator mechanism on the ORSA can be adjusted to open and separate horizontally the two ovoids and lock at the desired position with a locking knob. The inflatable ovoids can be filled with a mixture of saline, and 2% iodinated contrast solution through the luer lock for each ovoid. In some embodiments the ovoids are filled symmetrically. The saline volume will be dependent on the size of the fornices, and vaginal distal circumferential diameter. The inflatable ovoids are preferably made such that there is at least one cm distance posteriorly from the end of the catheter to the surface of the vaginal mucosa, thus lowering the dose to the vaginal mucosa and rectum. The adjustable volume of the ovoids and bigger diameter will conform to the shape of the fornices and improve the percentage depth dose to the tumor under treatment. The pivoting tandem mechanism can be fixed so the tandem bisects the ovoids and remains locked using a side locking knob. The square-shaped or flattened portion of the tandem is placed in the ovoid tract having a similar square-shaped or flattened configuration. This acts to limit the tandem from unwanted rotation in the uterine canal. Other shapes can be used to limit rotation of the tandem.

The two inflatable retractors are filled with saline to retract the anterior and posterior wall of the vaginal canal from the plane of the implant. The retractors can be filled symmetrically in some embodiments. The volume of the saline is adjusted to preferably have at least two cm retraction from the plane of the tandem. An advantage of an embodiment wherein the inflatable retractors are made of soft polyurethane semi-cylindrical or disc-shaped balloons is that the patient will feel less pain and little pressure. Since insertion of the tandem is followed by the insertion of the assembled single piece ovoid and retractor assembly, the implant time is much shorter compared with devices that require assembly of several components in the patient. Accordingly, patient discomfort and pain is minimal, lowering the need for complete and prolonged anesthetics. Due to adjustable features of the applicator, most of the positioning and adjustments is done remotely outside uterus, cervix, and vagina, making it minimally invasive, lowering patient pain and discomfort and number of personnel required for assistance.

In some embodiments, the applicator is designed to have markers every one centimeter for radiographic identification and has magnification factors readily available for dose calculations. The disposable material made of high strength plastics (Peek, GlassPeek, Carbon Fiber) or lightweight stainless steel has minimal radiation self absorption, removing the need for dosimetry corrections. The total length of the three catheters is preferably substantially identical to limit human errors during dosimetry calculations. In one embodiment, the applicator is designed such that the right ovoid will be connected through a transfer guide tube to channel one, the left ovoid to channel two, and the tandem to channel three of a commercially available 192-Ir HDR afterloader. In some embodiments, the tandem and ovoid system preferably comprises CT and MRI friendly material, making 3D dosimetry possible with no image artifacts.

Once the applicator is removed, the patient can then be allowed to heal. Advantageously, with the use of the applicator systems described herein, the recovery time is reduced compared to conventional treatments due to the improved dosimetry and limited invasiveness of the treatment.

Additional Features and Advantages of Some Embodiments

FIGS. 15-18 illustrate another assembled minimally invasive intracavitary brachytherapy applicator system according to embodiments of the present application. The applicator system of FIGS. 15-18 is similar in some respects to the systems and embodiments illustrated and described with reference to FIGS. 1-14. Some additional features and advantages are described below.

With reference to FIGS. 15-18, according to some embodiments, systems for treating cervical and/or uterine cancers in brachytherapy with an intracavitary brachytherapy applicator 200 comprise a tandem 202 adapted for insertion into a cervix of a patient. The tandem 202 can comprise an endoscopic viewing element 204 to facilitate treatment and one or more radiographic markers 206.

An ovoid assembly 210 comprises first and second adjustably inflatable ovoids 212, 214 and an ovoid support mechanism 216. The ovoid support mechanism 216 is adapted to support the ovoids 212, 214 and to allow for user manipulation to control the relative position of the ovoids for insertion of the ovoids within the fornices of a patient. The first and second adjustably inflatable ovoids 212, 214 have a deflated configuration for insertion into a patient and one or more adjustably inflated configurations for positioning the ovoid assembly during treatment. The first and second ovoids 212, 214 may have one or more radiographic markers. The ovoid assembly 210 comprises a tandem connector 224 adapted to releasably and adjustably couple the tandem 202 to the ovoid assembly 210 to allow for pivotal and translational motion of the tandem 202 relative to the ovoid assembly 210 and to limit rotational movement of the tandem 202 about a longitudinal axis of the tandem.

First and second adjustably inflatable retractors 230, 232 are adapted to be releasably coupled to the ovoid assembly at first and second retractor connector portions 234, 236. The first and second inflatable retractors 230, 232 have a deflated configuration for insertion into a patient and an adjustably inflated configuration for retraction of tissue during treatment. The first retractor 230 is adapted to be positioned to retract the bladder of a patient during treatment and the second retractor 232 is adapted to be positioned to retract the rectum of a patient during treatment. The tandem 202 and the first and second inflatable ovoids 212, 214 are adapted to be coupled to a radioactive source to deliver an implant radiation dose suitable for cancer treatment at a cancerous cervical treatment site in a patient.

Some embodiments are described in more detail below. The applicator systems and methods can have one or more of the following advantageous characteristics in some embodiments. For example, the applicator system of FIGS. 15-18 preferably has a configuration that makes the applicator system easier to implant, less invasive and traumatic for the patient, or provides improved inter-fraction implant geometric reproducibility by including one or more of the following features and functionalities in the system.

The ovoid support mechanism 216 is adapted to support the ovoids 212, 214 and to allow for user manipulation to control the relative position of the ovoids for insertion of the ovoids within the fornices of a patient. The ovoid support mechanism 216 supports first and second catheter shafts 240, 242 coupled with the ovoids for delivering radiation to the ovoids. The ovoid support mechanism 216 also comprises first and second handle portions 244, 246 coupled for pivotal movement relative to one another. Movement of the handle portions 244, 246 relative to each other controls the distance between the first and second ovoids 212, 214. The ovoid support mechanism 216 comprises a threaded shaft 248 extending between the first and second handle portions 244 and 246. An adjustment wheel 249 is coupled to a central portion of the threaded shaft 248.

The first and second handle portions 244 and 246 comprise first and second knobs 258, 259 coupled to the handle portions and configured to be coupled to the threaded shaft 248. In some embodiments the knobs comprise tabs or levers that are pivotally coupled to the handle portions and that are disposed in a first configuration wherein a spring 261 located between the handle portion and a proximal portion of the knob urges a distal portion of the knob into engagement with the threaded shaft 248. With the knobs in the first engaged configuration, the adjustment wheel 249 can be rotated by a user. Rotation of the threaded shaft 248 provides for fine adjustment to move the handle portions toward or away from each other, to precisely control the relative movement, position, and separation of the of the ovoids 212, 214. Additionally, the knobs have a second unengaged configuration. A user can press down on a proximal portion of the tab or lever against the spring force such that a distal portion of the knob disengages with the threaded shaft. In the disengaged configuration, the user is free to make large adjustments to the movement, position and separation of the ovoids by moving the handle portions toward or away from each other. Thus, the threaded shaft and knob features provide for quick and large adjustments in position by disengaging the knob from the threaded shaft, while allowing for precise control over the movement and positioning of the ovoids in an engaged configuration when the knob features are released and the spring forces the knob features into engagement with the threaded shaft. The relative position of the handle portions 244, 246 can be fixed relative to the ovoid support mechanism 216 by releasing or positioning the knobs to allow the knobs to engage with the threaded shaft 248. Accordingly, in some embodiments, the two knobs on the ovoid handles can be pressed to allow the two ovoid balloons to be separated horizontally in a coarse adjustment mode. In some embodiments, the adjustment wheel between the two ovoid handles allows the two ovoid balloons to be adjusted horizontally in a fine adjustment mode.

A lower portion of the ovoid support mechanism 216 comprises the tandem connector 224. In some embodiments, the tandem connector is a flexible clip. The tandem connector 224 preferably comprises a slot 252 for receiving the tandem 202. In some embodiments, the tandem connector has a generally horse-shoe-shaped cross-section. The tandem connector can be configured to grip the tandem to allow for translational and pivotal coupling of the tandem to the ovoid support mechanism.

The tandem connector 224 is preferably coupled to the ovoid support mechanism 216 such that the tandem connector can pivot relative to the ovoid support mechanism in some configurations and be clamped in position in other configurations. In some embodiments, the ovoid support mechanism comprises one or more handles 265, 267 operatively coupled with the tandem connector. When the one or more handles are positioned in a first open configuration, the tandem connector 224 can receive and hold a tandem and allow for movement of the tandem distally and proximally, and also allow for pivotal movement of the tandem and tandem connector relative to the ovoid support mechanism. The configuration of the tandem connector when engaged with the tandem preferably limits rotation of the tandem about a longitudinal axis of the tandem. When the one or more handles are positioned in a second clamped position, the tandem connector is compressed within the ovoid support mechanism 216 such that the tandem connector and tandem are generally held in position to limit movement distally or proximally, and to limit pivotal movement. Accordingly, positioning and adjustment of the tandem relative to the ovoid support mechanism is facilitated with the one or more handles in an open configuration and when a desired positioning has been achieved by the user, the one or more handles can be moved to the closed configuration to hold the tandem in the desired orientation.

Figure 16:
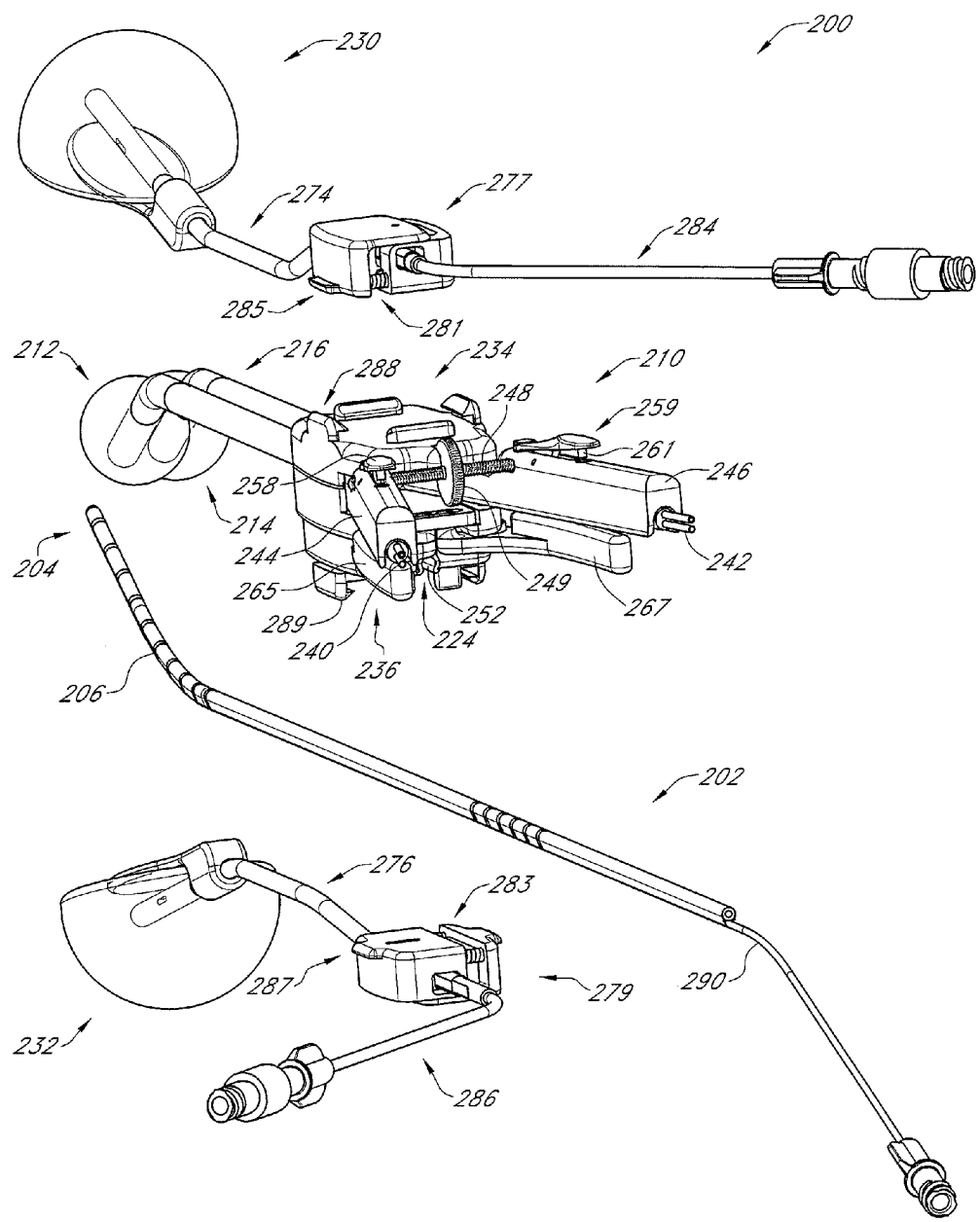
FIG. 16 illustrates an exploded view of the applicator system of FIG. 15.
Figure 17:
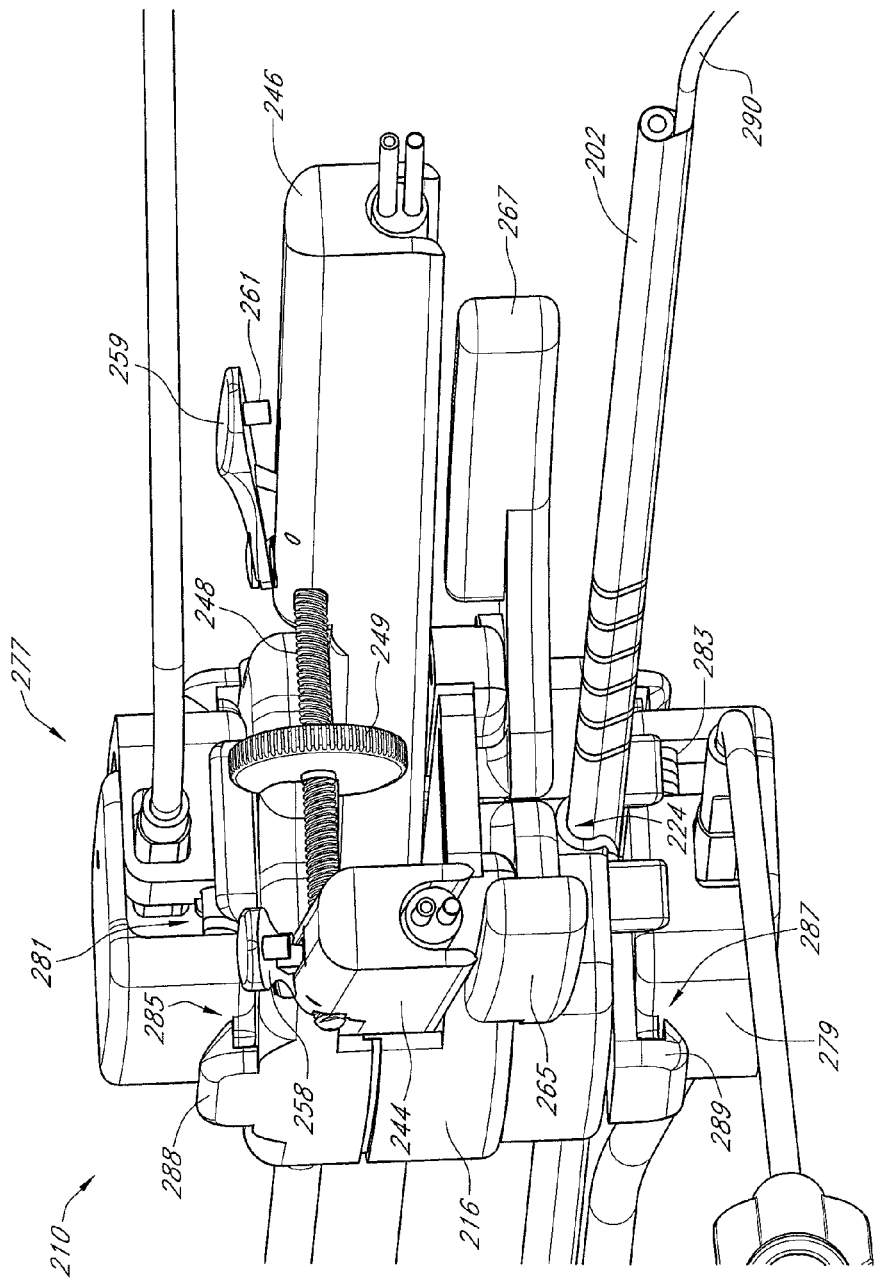
FIG. 17 illustrates rear side perspective view of the applicator system of FIG. 15 according to embodiments of the present application.
Figure 18:
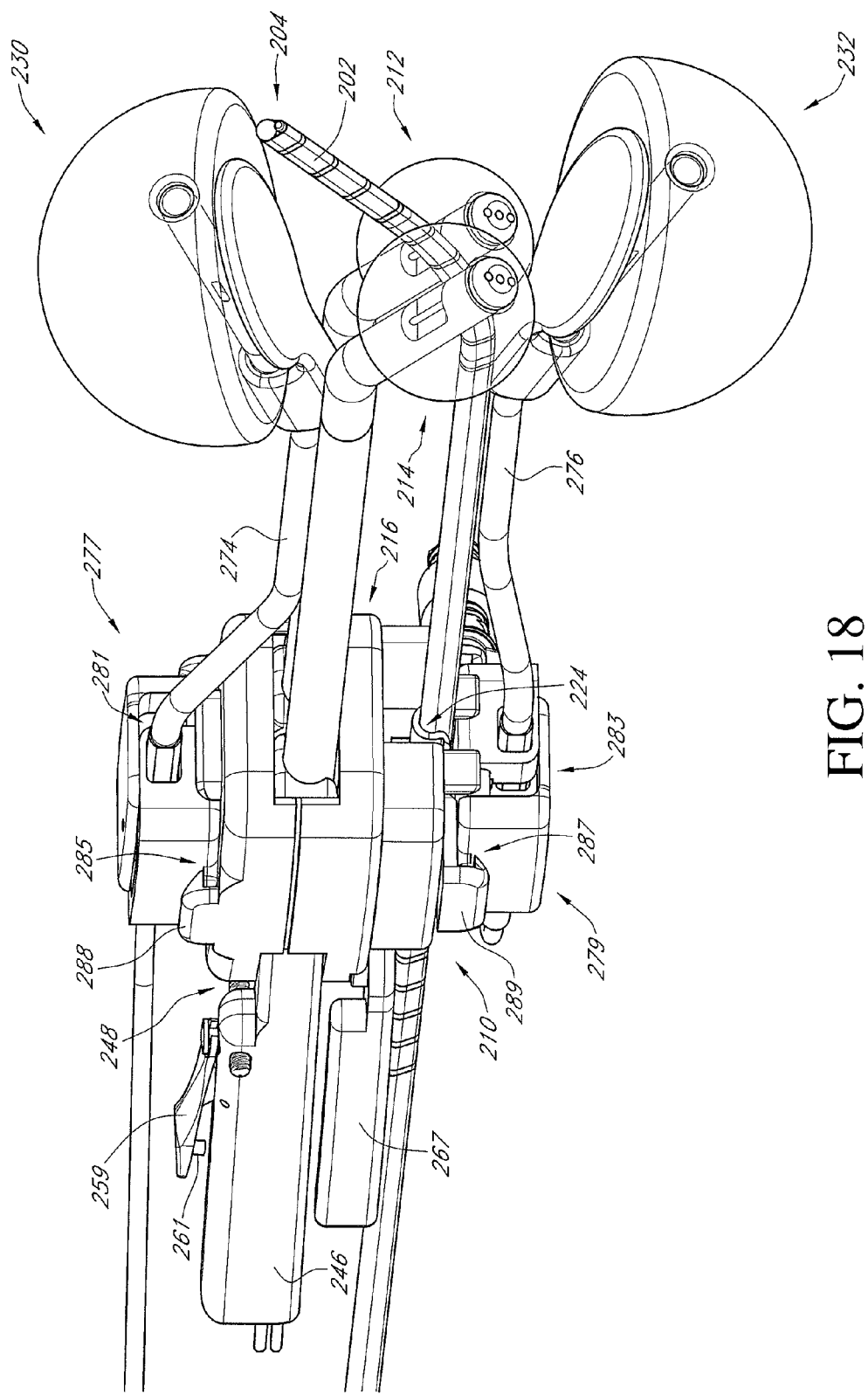
FIG. 18 illustrates a front side perspective view of the applicator system of FIG. 15 according to embodiments of the present application.

As mentioned above, a tandem connector 224 mechanism is provided for coupling the tandem 202 with the ovoid assembly 210. The mechanism preferably enables the tandem 202 to pivot in the anterior/posterior direction about a point in reference to the ovoids 212, 214 using a clip and clamping mechanism within the ovoid assembly 210 to interface with the tandem as best seen in FIGS. 16-18. The mechanism also preferably allows the user to translate and/or pivot the tandem to keep it at the mid-plane of the ovoids 212, 214 during treatment. Enabling the user to position the tandem 202 to bisect the ovoids 212, 214 helps to improve implant geometry and dose distribution. In some embodiments, the tandem is arranged to limit inadvertent rotation of the tandem 202 during manipulation and treatment. Accordingly, the mechanism preferably limits the tandem from rotation around a longitudinal axis of the tandem and permits translational and pivotal motion to achieve an advantageous mid-plane position relative to the ovoids 212, 214.

Retractor balloons 230, 232 are preferably added to the intracavitary brachytherapy applicator 200 to retract the bladder and the rectum from the radiation sources, thus lowering the dose to these critical structures. This can reduce, and in some cases eliminate, the need to use of vaginal packing after the applicator is in place. The retractor balloons 230, 232 are coupled to catheters 284, 286 that are preferably anchored on the ovoid assembly 210. The retractor balloons 230, 232 are preferably inflated with saline. Other suitable inflation mediums can also be used. The balloons can be hemispherical when inflated to push the vaginal mucosa, bladder, and rectum away from the radiation site. Balloons having other suitable shapes and sizes for providing retraction can also be used. The retraction mechanism is preferably inflatable to retract the bladder and the rectum by at least about 2 cm away from a plane of the implant defined at the plane of the tandem bisecting the ovoids. The retraction mechanism preferably retracts equidistance from the plane of the implant. The retraction mechanism comprises balloons 230, 232 and retractor supports 274, 276 coupled to the ovoid assembly 210 at retractor connection portions 234, 236. The bladder and rectum retractor balloons preferably have attachment mechanisms 277, 279 that allow for the lengths of the retractor supports 274, 276 to be adjusted. By pressing a spring actuated lock mechanism 281, 283 on the attachment mechanisms 277, 279, the retractor supports 274, 276 can be moved proximally or distally relative to the attachment mechanisms for the desired length corresponding to the length of the vaginal canal. When the spring actuated lock mechanism 281, 283 is released, the retractor supports 274, 276 are held in position and preferably do not move proximally or distally while in the locked position. After insertion of the retractor, the attachment mechanism 277, 279 can be removably coupled to the ovoid assembly 210. In some embodiments, the attachment mechanism can be coupled to the ovoid assembly by pressing the attachment mechanism against the ovoid assembly 210. The ovoid assembly preferably has tabs 285, 287 that engage with tabs 288, 289 on the attachment mechanism 277, 279. As the attachment mechanism is pressed against the ovoid assembly, the tabs 288, 289 on the ovoid assembly preferably engage the tabs 285, 283 on the attachment mechanism such that the spring actuated lock mechanism 281, 283 compresses to allow the tabs on the attachment mechanism snap into place between the tabs on the ovoid assembly and a surface of the ovoid assembly in a configuration similar to a key-lock attachment. Both the bladder and the rectal balloons can have similar attachment configurations to adjust for the length of the vaginal canal by pressing the spring-actuated locking mechanism similar to a key-lock attachment. In some embodiments, the bladder retractor is preferably filled with air or a gas to push away the bladder from the radiation sources. Compared with a liquid, this may limit the retractor from leaning over the tandem and ovoid due to its weight or gravity to displace or change its optimal geometry. The rectum retractor is preferably filled with saline to push away the rectum from the source of radiation. The saline weight due to gravity will push away the rectum from the sources of radiation. In some embodiments, both retractors are suitable to be filled with either a gas or a liquid, such as for example, air or saline.

With reference to FIGS. 15-18, in some embodiments, a miniaturized endoscopic fiber optic bundle 290 is integrated with the tandem 202. In some embodiments, the fiber optic bundle 290 can be about 1 mm thick along the length of the tandem 202. An endoscope can be illuminated by a battery operated LED light and connected to a CMOS or a CCD camera. In some embodiments, the tandem may have a high resolution fiber optic bundle of up to 10000 pixels, or more, for finding the cervical os, connected to a CCD or CMOS high resolution camera. The CCD or CMOS camera output may be connected to a laptop computer via USB2 or USB3 connector, or another connector, or wirelessly connected, to display static and/or video images of the cervix, cervical os, and uterine canal. The camera may be used for image guidance to find the cervical os, or to guide the tandem into the uterine canal all the way to the end without perforating the uterus. In some embodiments, an alternative configuration to the optical fiber bundle-camera is a miniaturized ultrasound transducer to perform these or other functions and that is configured to be attached to a display to view the ultrasound pictures of the cervical os, uterine canal, and evaluate the extent of disease or response to cancer to treatments.

Visualization capabilities of the tandem 202 enables the physician to find the cervical os, guide the tandem into the cervical os and uterine canal, sound the uterus, and inspect the extent of the disease in vagina, cervix, uterine canal, and the uterus. The visualization can help the radiation oncologist to guide the tandem to the end of the uterine canal without perforating it. A mechanism, such as markings on the tandem 206, can be used to measure the length of the uterine canal from the cervical os to the end of the canal. This feature helps sound the uterine canal and position the flange on the tandem to limit the risk of the tandem perforating the uterus.

In some embodiments, methods of using the applicator 200 are similar to methods described previously in connection with other embodiments. With reference to FIGS. 15-18, in some embodiments, handles on the ovoid assembly can be adjusted to open and separate horizontally the two ovoids and lock at the desired position. In some embodiments, the two knobs on the ovoid handles can be pressed to allow the two ovoid balloons to be separated horizontally in a coarse adjustment mode. In some embodiments, the adjustment wheel between the two ovoid handles allows the two ovoid balloons to be adjusted horizontally in a fine adjustment mode. The inflatable ovoids can be filled with a fluid. The pivoting tandem mechanism can be adjusted or fixed so the tandem bisects the ovoids and remains locked using a tandem handle clamping mechanism. The two inflatable retractors are filled with fluid to retract the anterior and posterior wall of the vaginal canal from the plane of the implant. The length and positioning of the retractors can be adjusted by pressing the spring actuated lock mechanism and manipulating the retractor supports to the desired length relative the attachment mechanism. The attachment mechanism for the retractor can be pressed against the ovoid assembly to snap the retractors into position. Due to adjustable features of the applicator, most of the positioning and adjustments is done remotely outside uterus, cervix, and vagina, making it minimally invasive, lowering patient pain and discomfort and number of personnel required for assistance. Visualization of the procedure can be made as described above. Once the applicator is removed, the patient can then be allowed to heal. Advantageously, with the use of the applicator systems described herein, the recovery time is reduced compared to conventional treatments due to the improved dosimetry and limited invasiveness of the treatment.

It will be apparent to those skilled in the art that various modifications and variations can be made in the present embodiments and methods without departing from the scope or spirit of the advantages of the present application. Thus, it is intended that the present application cover the modifications and variations of these embodiments and their equivalents.

What is claimed is:

1. A method for treating cervical and/or uterine cancers in brachytherapy with an intracavitary brachytherapy applicator, comprising:
   inserting a tandem into a cervix of a patient, wherein the tandem comprises an endoscopic viewing element and a radiographic marker;
   providing an ovoid assembly, wherein the ovoid assembly comprises first and second adjustably inflatable capless colpostats and an ovoid support mechanism;
   simultaneously inserting into the patient the first and second adjustably inflatable capless colpostats in a deflated configuration as integrated pieces of a single unit during treatment and manipulating the ovoid support mechanism to control the relative position of the colpostats within the fornices of the patient, wherein the first and second adjustably inflatable capless colpostats have the deflated configuration for insertion into a patient and an adjustably inflated configuration for positioning the ovoid assembly during treatment;
   delivering fluid through a first inflation catheter shaft at least partially housed in a first handle portion of the ovoid assembly to inflate the first adjustably inflatable capless colpostat;
   delivering fluid through a second inflation catheter shaft at least partially housed in a second handle portion of the ovoid assembly to inflate the second adjustably inflatable capless colpostat;
   releasably and adjustably coupling the tandem to a tandem connector of the ovoid assembly to allow for pivotal and translational motion of the tandem relative to the ovoid assembly and to limit rotational movement of the tandem about a longitudinal axis of the tandem;
   coupling the tandem and the first and second inflatable capless colpostats to a radioactive source to deliver an implant radiation dose suitable for cancer treatment at a cancerous cervical and/or uterine treatment site in a patient, wherein the first handle portion of the ovoid assembly at least partially houses a radiation transfer catheter shaft for delivering radiation to the first adjustably inflatable capless colpostat, and wherein the second handle portion of the ovoid assembly at least partially houses a radiation transfer catheter shaft for delivering radiation to the second adjustably inflatable capless colpostat.

2. The method of claim 1, wherein the first and second adjustably inflatable capless colpostats are configured such that there is one centimeter distance posteriorly from an end of a catheter of the ovoid assembly, to a surface of the adjustably inflatable capless colpostats adapted to be positioned adjacent a surface of the vaginal mucosa, when inflated and in use.

3. A method for treating cervical and/or uterine cancers in brachytherapy with an intracavitary brachytherapy applicator, comprising:
   inserting a tandem into a cervix of a patient;
   providing an ovoid assembly comprising first and second inflatable capless colpostats and an ovoid support mechanism, the ovoid support mechanism comprising first and second handles wherein the handles are configured to allow for user manipulation to control the relative position of the capless colpostats using a coarse adjustment mechanism in a first configuration and using a fine adjustment mechanism in a second configuration;
   simultaneously inserting into the patient the first and second inflatable capless colpostats in a deflated configuration as integrated pieces of a single unit during treatment;
   inserting the first and second inflatable capless colpostats within fornices of a patient, wherein the ovoid support mechanism supports the capless colpostats and allows for user manipulation to control the relative position of the capless colpostats for insertion of the capless colpostats within the fornices of a patient;
   delivering fluid through an inflation catheter shaft within the first handle to control inflation of the first inflatable capless colpostat, and delivering fluid through an inflation catheter shaft within the second handle to control inflation of the second inflatable capless colpostat; and
   coupling first and second retractors to the ovoid assembly, wherein the first retractor retracts the bladder of a patient during treatment and the second retractor retracts the rectum of a patient during treatment;
   coupling the tandem and the first and second inflatable capless colpostats to a radioactive source to deliver an implant radiation dose suitable for cancer treatment at a cancerous cervical and/or uterine treatment site in a patient, wherein the first handle at least partially houses a radiation transfer catheter shaft for delivering radiation to the first inflatable capless colpostat, and wherein the second handle at least partially houses a radiation transfer catheter shaft for delivering radiation to the second inflatable capless colpostat.

4. The method of claim 3, wherein the tandem comprises an endoscopic viewing element and further comprising using the viewing element to facilitate positioning of the tandem.

5. The method of claim 3, wherein the ovoid assembly comprises a tandem connector and further comprising releasably and adjustably coupling the tandem to the ovoid assembly with the tandem connector.

6. The method of claim 3, wherein the ovoid assembly comprises a tandem connector and further comprising pivotally moving the tandem relative to the ovoid assembly using the tandem connector.

7. The method of claim 3, wherein the ovoid assembly comprises a tandem connector and further comprising translationally moving the tandem relative to the ovoid assembly using the tandem connector.

8. The method of claim 3, wherein the ovoid assembly comprises a tandem connector and further comprising limiting rotational movement of the tandem about a longitudinal axis of the tandem using the tandem connector.

9. The method of claim 3, further comprising releasably coupling the first and second retractors to the ovoid assembly.

10. The method of claim 3, wherein the first and second inflatable capless colpostats are configured such that there is one centimeter distance posteriorly from an end a catheter of the ovoid assembly, to a surface of the inflatable capless colpostats adapted to be positioned adjacent a surface of the vaginal mucosa, when inflated and in use.

11. A method for treating cervical and/or uterine cancers in brachytherapy with an intracavitary brachytherapy applicator, comprising:
inserting a tandem into a cervix of a patient;
providing an ovoid assembly comprising first and second inflatable capless colpostats and an ovoid support mechanism;
simultaneously inserting into the patient the first and second inflatable capless colpostats in a deflated configuration as integrated pieces of a single unit during treatment;
inserting the first and second inflatable capless colpostats within fornices of a patient;
releasably and adjustably coupling the tandem to a tandem connector of the ovoid assembly, wherein the ovoid assembly comprises a first configuration wherein one or more handles coupled to the tandem connector are in an open position and adapted for pivotal and translational movement of the tandem, and a second configuration wherein the one or more handles coupled to the tandem connector are in a closed position and adapted to clamp the tandem connector to limit movement of the tandem, wherein the one or more handles at least partially house one or more inflation catheter shafts for delivering fluid to control inflation of one or more of the first and second inflatable capless colpostats; and
coupling first and second retractors to the ovoid assembly, wherein the first retractor retracts the bladder of a patient during treatment and the second retractor retracts the rectum of a patient during treatment;
coupling the tandem and the first and second inflatable capless colpostats to a radioactive source to deliver an implant radiation dose suitable for cancer treatment at a cancerous cervical and/or uterine treatment site in a patient, wherein the one or more handles at least partially house one or more radiation transfer catheter shafts for delivering radiation to one or more of the first and second inflatable capless colpostats.

12. The method of claim 11, wherein the tandem comprises an endoscopic viewing element and further comprising using the viewing element to facilitate positioning of the tandem.

13. The method of claim 11, wherein the ovoid support mechanism supports the capless colpostats and allows for user manipulation to control the relative position of the capless colpostats for insertion of the capless colpostats within the fornices of a patient.

14. The method of claim 11, further comprising adjustably inflating the first and second inflatable capless colpostats after insertion into a patient.

15. The method of claim 11, further comprising releasably coupling the first and second retractors to the ovoid assembly.

16. The method of claim 11, further comprising inflating the first and second retractors.

17. The method of claim 11, further comprising adjustably inflating the first and second retractors.

18. The method of claim 11, wherein the first and second inflatable capless colpostats are configured such that there is one centimeter distance posteriorly from an end of a catheter of the ovoid assembly, to a surface of the inflatable capless colpostats adapted to be positioned adjacent a surface of the vaginal mucosa, when inflated and in use.

\* \* \* \* \*